United States Patent
Antony Prince

(10) Patent No.: US 11,530,178 B2
(45) Date of Patent: Dec. 20, 2022

(54) HYPER-BRANCHED COMPOUNDS, SYNTHESIS AND USES THEREOF

(71) Applicant: MEMSIFT INNOVATIONS PTE. LTD., Singapore (SG)

(72) Inventor: James Selvaraj Antony Prince, Singapore (SG)

(73) Assignee: MEMSIFT INNOVATIONS PTE. LTD., Singapore (SG)

( * ) Notice: Subject to any disclaimer, the term of this patent is extended or adjusted under 35 U.S.C. 154(b) by 171 days.

(21) Appl. No.: 16/961,946

(22) PCT Filed: Jan. 18, 2019

(86) PCT No.: PCT/SG2019/050032
§ 371 (c)(1),
(2) Date: Jul. 14, 2020

(87) PCT Pub. No.: WO2019/143299
PCT Pub. Date: Jul. 25, 2019

(65) Prior Publication Data
US 2020/0385338 A1    Dec. 10, 2020

(30) Foreign Application Priority Data
Jan. 18, 2018 (IN) ............................. 201841002063

(51) Int. Cl.
*C07C 233/66* (2006.01)
*B01D 61/36* (2006.01)
*B01D 71/34* (2006.01)

(52) U.S. Cl.
CPC .......... *C07C 233/66* (2013.01); *B01D 61/364* (2013.01); *B01D 71/34* (2013.01)

(58) Field of Classification Search
None
See application file for complete search history.

(56) References Cited

FOREIGN PATENT DOCUMENTS

| CN | 105413494 A | 3/2016 |
| CN | 107501500 A | 12/2017 |
| KR | 1020130098090 A | 9/2013 |

OTHER PUBLICATIONS

Hagooly et al., Toward the Synthesis of the Rare N-(Trifluoromethyl)amides and the N-(Difluoromethylene)-N-(trifluoromethyl)amines [RN(CF3)CF2R'] Using BrF3. The Journal of Organic Chemistry, Oct. 16, 2009, vol. 74, No. 22, pp. 8578-8582.

Xu et al., Construction of hydrophobic surfaces on polyvinylidene fluoride film and cotton fabric using perfluorohexane functionalized carbon nanotubes and graphene oxide. Textile Research Journal, Aug. 17, 2016, vol. 87, No. 16, pp. 2005-2017.

(Continued)

*Primary Examiner* — Sudhakar Katakam
*Assistant Examiner* — Jennifer C Sawyer
(74) *Attorney, Agent, or Firm* — Burns & Levinson LLP; Steven M. Mills

(57) ABSTRACT

The present invention relates to hyper-branched compounds, a method of synthesizing the hyper-branched compounds and applications of the hyper-branched compounds. The hyper-branched compounds of the present invention include hyper-branched fluorinated compounds, hyper-branched fluorinated graphene and hyper-branched amine functionalized graphene oxide.

17 Claims, 19 Drawing Sheets

(56) References Cited

OTHER PUBLICATIONS

Lim et al., Cross-linked graphene oxide membrane having high ion selectivity and antibacterial activity prepared using tannic acid-functionalized graphene oxide and polyethyleneimine. Journal of Membrane Science, Aug. 31, 2016, vol. 521, pp. 1-9.
International Search Report for International Application No. PCT/SG2019/050032 dated Apr. 25, 2019.
Written Opinion for International Application No. PCT/SG2019/050032 dated Apr. 25, 2019.

$N^1,N^3,N^5$-tris(perfluoropropan-2-yl)-$N^1,N^3,N^5$-tris(2,4,5-trifluorophenyl)benzene-1,3,5-tricarboamide

HYPER-BRANCHED COMPOUNDS, SYNTHESIS AND USES THEREOF

CROSS REFERENCE TO RELATED APPLICATIONS

This application is a national stage application, filed under 35 U.S.C. § 371, of International Application No. PCT/SG2019/050032, filed Jan. 18, 2019, which claims priority to IN 201841002063, filed Jan. 18, 2018, each of which is incorporated herein by reference in its entirety.

TECHNICAL FIELD

The present invention generally relates to hyper-branched compounds, a method of synthesizing the hyper-branched compounds and applications of the hyper-branched compounds.

BACKGROUND OF THE INVENTION

The global water shortage crisis has become a critical issue, with about 1.1 billion people estimated to have limited access to clean water while about 2.4 billion people lack access to proper sanitation facilities (WHO, 2003). Fresh water shortage around the world is increasing at a rapid rate due to the human population growth and the scarcity of fresh water resources. Given the abundance of seawater on earth, it is therefore attractive to explore various seawater desalination technologies.

Current popular method of desalination is a pressure driven membrane-process reverse osmosis (RO). However, RO is limited by the salt concentration in the feed water whereby the technology can only recover 45-50% of the water from seawater due to osmotic strength. The conventional thermal desalination processes such as multi-stage flash (MSF), multiple effect evaporation (MEE), and thermal or mechanical vapor compression (VC) processes are too costly and energy-inefficient due to high energy consumption rates. Hence, despite all the available desalination process, an alternative desalination offering lower energy consumption is desired.

Membrane distillation (MD) is an emerging desalination technology that combines membrane and evaporation process. The MD process involves the use of a heat source to provide energy necessary to vaporize a liquid; the vapour molecules are then transported across pores of a hydrophobic microporous membrane and condensed on an opposite side of the membrane (Lawson & Llyod, 1997). The MD process can be operated using renewable energy such as solar energy, geothermal energy and low-grade waste heat from industrial processes. Thus, in comparison with seawater desalination technologies such as reverse osmosis or thermal processes, MD appears to be more promising because the MD process is relatively energy saving and low-cost. It is also worth noting that MD has a wide range of practical applications in various industrial sectors such as desalination, wastewater treatment, food & beverage, biomedical, semiconductor and electroplating industries.

Among the different types of MD configurations which are available, only 4 major configurations are used widely: direct contact membrane distillation (DCMD), air gap membrane distillation (AGMD), vacuum membrane distillation (VMD) and sweeping gas membrane distillation (SGMD). In the MD process, a porous hydrophobic membrane is brought into contact to separate a hot feed solution and a cold permeate. For efficient MD process, the membrane should ideally exhibit several optimum characteristics in terms of membrane thickness, membrane porosity, membrane pore size, chemical and thermal stability, membrane surface chemistry (hydrophobicity) and high liquid entry pressure (LEP).

Even though the MD technology exists since 1960s, MD has not been fully commercialized and widely used due to a key limiting factor that the membranes are wetted fairly easily, causing the membranes to lose their efficiency. The membranes are wetted when liquid penetrates into their pores or condensation occurs in the membrane matrix. The membrane pores are supposed to be occupied by water vapour, according to the theory behind MD. However, when liquids enter the pores or condensation occurs inside the membrane matrix, the membrane will be wetted which allows solute (salts) to pass through the membrane by diffusion.

Several methods have been explored to prevent membrane wetting. The current solution to wetting is to apply a finely porous hydrophobic coating, which helps to increase the membrane hydrophobicity while maintaining acceptable porosity. However, this reduces the pore size of the membrane, thus degrading performance.

It is therefore desirable to provide a compound and membrane that seeks to address at least one of the problems described hereinabove, or at least to provide an alternative.

SUMMARY OF THE INVENTION

The present invention provides hyper-branched compounds and a method of synthesizing the hyper-branched compounds. In some embodiments, the hyper-branched compounds of the present invention are highly fluorinated and may be used as a thermally stable, hydrophobic additive in a MD membrane. Dependent on terminal chemical group of the branches of the hyper-branched compounds, the properties of the hyper-branched compounds may be tuned for diverse applications.

In accordance with a first aspect of this invention, a hyper-branched compound represented by the general structure (I) is provided:

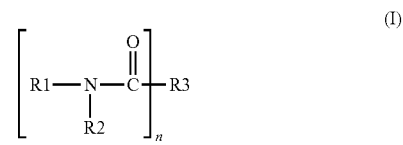

wherein n is an integer representing the number of repeat units and wherein the integer is 1 to 3;

R2 is a fluorinated hydrocarbon having the following structure:

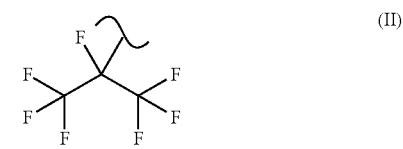

R1 is a fluorinated phenyl; and

R3 is a phenyl substituted with the n repeat units when n is 2 or 3, or a phenyl substituted with one or more fluorine when n is 1.

In accordance with one embodiment of this invention, R1 is fluorinated phenyl selected from the group consisting of 3,5-bis(trifluoromethyl)phenyl and 2, 4, 5-trifluorophenyl. R3 is phenyl substituted at positions 2, 4, 5 with fluorine and substituted at position 3 with —OCH$_3$, when n is 1.

In accordance with a second aspect of this invention, a method of preparing a hyper-branched compound represented by the general structure (I) is provided:

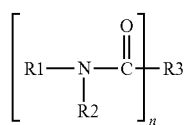

(I)

The method comprises contacting a fluorinated first reactant containing at least one primary amine group with a fluorinated second reactant containing at least one amine reactive group in the presence of a solvent to form a fluorinated intermediate containing at least one secondary amine group; and contacting the fluorinated intermediate with a third reactant containing at least one carbonyl chloride group to form at least one amide linkage between the fluorinated intermediate and the third reactant to form a fluorinated amide-containing compound comprising n repeat units, wherein n is 1 to 3.

In accordance with some embodiments of this invention, the amine reactive group is iodine. The first reactant is fluorinated aniline. The second reactant is heptafluoro-2-iodopropane. The third reactant is selected from the group consisting of trimesoyl chloride and 2,4,5-trifluoro-3-methoxybenzoyl chloride.

In accordance with a third aspect of this invention, another hyper-branched compound having the following general structure (I) is provided:

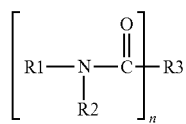

(I)

wherein n denotes an integer representing the number of repeat units and the integer is >1;

R2 is a fluorinated alkyl amine;

R1 is hydrogen; and

R3 is a graphene functionalized with n repeat units.

In accordance with another embodiment of this invention, R2 is a tertiary amine, R1 is a hydrogen; and R3 is a graphene oxide functionalized with n repeat units.

In accordance with some embodiments of this invention, the hyper-branched compounds of the present invention include hyper-branched fluorinated compounds, hyper-branched fluorinated graphene and hyper-branched amine functionalized graphene oxide.

In accordance with a fourth aspect of this invention, a method of preparing a casting solution comprising a hyper-branched compound is provided. The method comprises (a) adding a first reactant to a solvent to obtain a solution, wherein the first reactant comprises at least one primary amine group; (b) adding a second reactant to the solution, wherein the second reactant comprises at least one amine reactive group to form an intermediate comprising at least one secondary amine group; (c) adding a third reactant to the solution, wherein the third reactant comprises at least one carbonyl chloride group to form at least one amide linkage between the intermediate and the third reactant to form a hyper-branched compound with n repeat units, wherein n is 1 to 3 or >1; and (d) adding a base polymer to the solution to form a casting solution.

In accordance with some embodiments of this invention, the steps (b) to (d) are carried out at a temperature between 50 to 70° C., at a stirring speed between 200-300 rpm.

In accordance with some embodiments of this invention, the base polymer is polyvinylidene fluoride.

In accordance with some embodiments of this invention, the method further comprises using the casting solution to fabricate a membrane via phase inversion method.

DETAILED DESCRIPTION OF THE INVENTION

Figure 1:
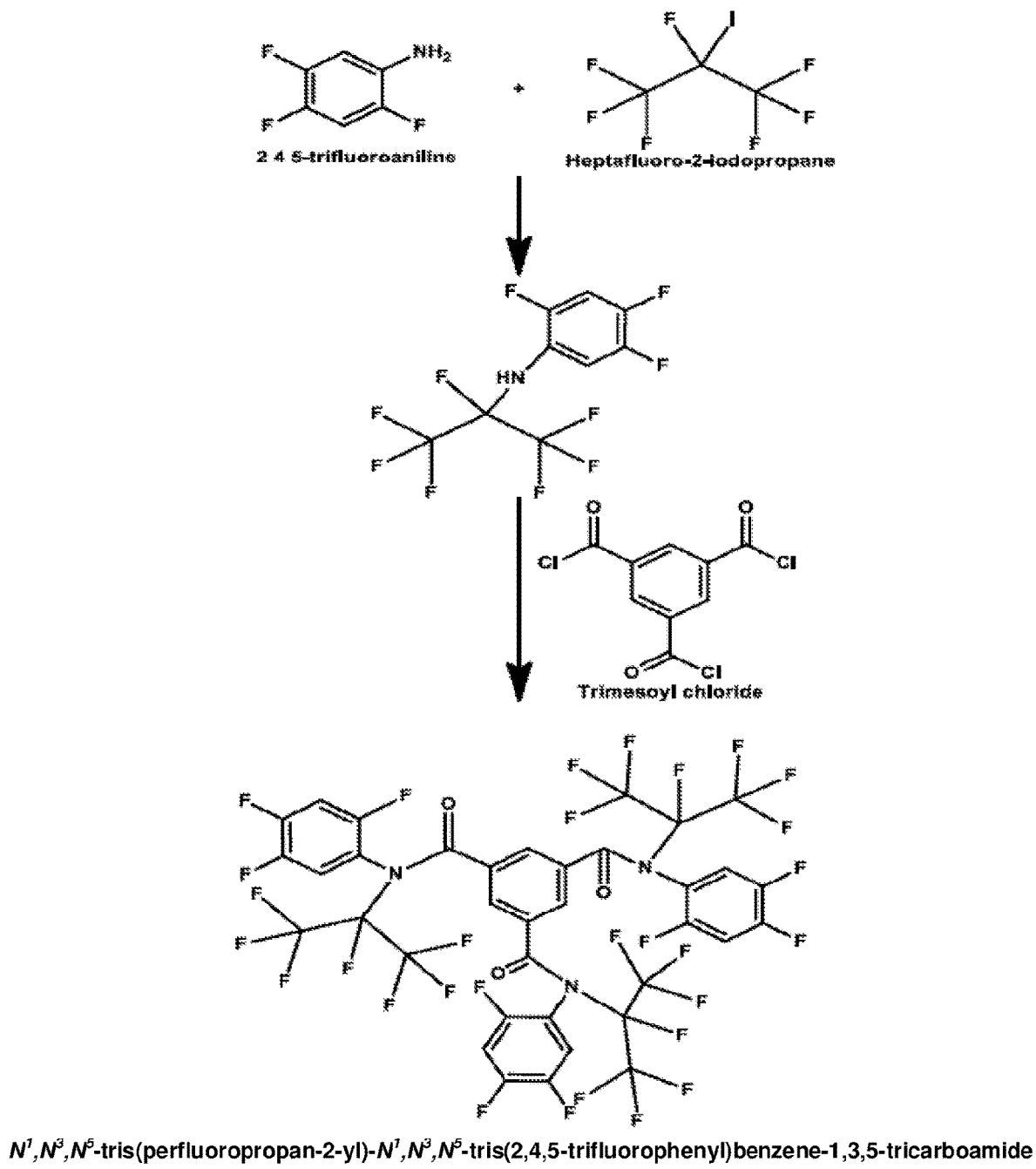
FIG. 1 shows a reaction scheme for preparing a hyper-branched compound in accordance with one embodiment of the invention.

The hyper-branched compounds of the present invention, method of preparation and applications thereof are presented, followed by exemplary embodiments given in the ensuing examples. It should be noted that the examples are provided solely to aid understanding of the present invention and should not be interpreted to be limiting the scope of the present invention. The skilled person in the art may modify or combine features from various embodiments in the spirit of the present invention. Such modifications are also considered to fall within the scope of the present invention.

In a first aspect, a hyper-branched compound represented by the general structure (I):

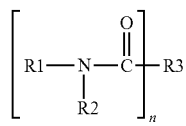

(I)

is provided, wherein n is an integer representing the number of repeat units and wherein the integer is 1 to 3;

R2 is a fluorinated hydrocarbon having the following structure:

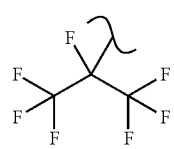

(II)

R1 is a fluorinated phenyl; and

R3 is a phenyl substituted with the n repeat units when n is 2 or 3, or a phenyl substituted with one or more fluorine when n is 1.

In some embodiments, R1 is a fluorinated phenyl selected from the group consisting of 3, 5-bis(trifluoromethyl)phenyl and 2, 4, 5-trifluorophenyl.

When R1 is 3, 5-bis(trifluoromethyl)phenyl and n is 3, the compound is $N^1,N^3,N^5$-tris(3,5-bis(trifluoromethyl)phenyl)-$N^1,N^3,N^5$-tris(perfluoropropan-2-yl)benzene-1,3,5-tricarboxamide represented by the following structural formula (A):

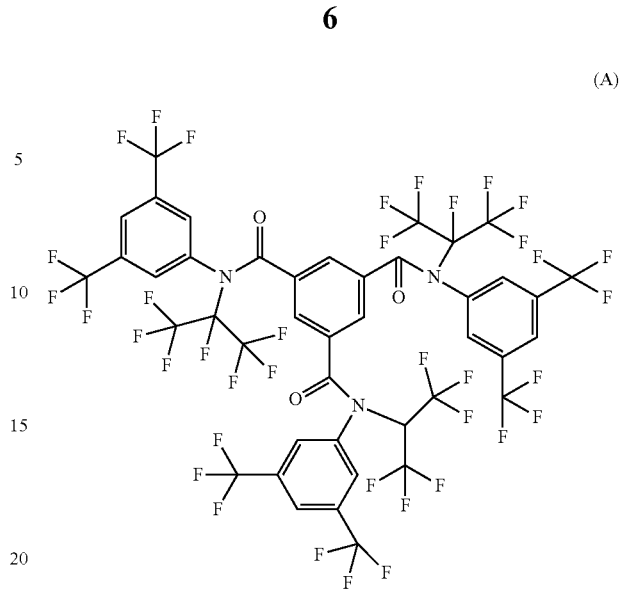

(A)

When R1 is 2, 4, 5-trifluorophenyl and n is 3, the compound is $N^1,N^3,N^5$-tris(perfluoropropan-2-yl)-$N^1,N^3,N^5$-tris(2,4,5-trifluorophenyl)benzene-1,3,5-tricarboamide, represented by the following structural formula (B):

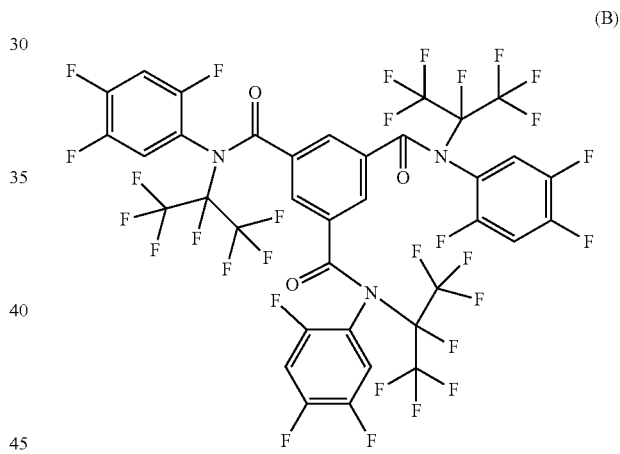

(B)

In one embodiment, when n is 1, R3 is a phenyl substituted at positions 2, 4, 5 with fluorine and substituted at position 3 with —OCH$_3$. The compound of this embodiment is 2,4,5-trifluoro-3-methoxy-N-(perfluoropropan-2-yl)-N-(2,4,5-trifluorophenyl)benzamide, represented by the following structural formula (C):

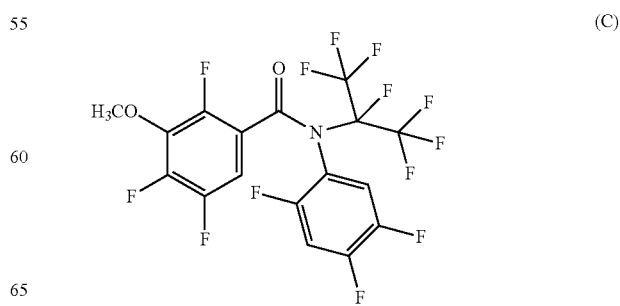

(C)

The hyper-branched compounds of the present invention are compounds that are generally prepared from at least a first reactant comprising at least one primary amine group, $R^1$—$NH_2$; and a second reactant comprising at least one amine reactive group.

The first reactant is reacted with the second reactant in the presence of a suitable solvent whereby the primary amine group on the first reactant reacts with the amine reactive group on a molecule of the second reactant to form a secondary amine linkage between the first reactant and the second reactant. Depending upon the number of primary amine group and amine reactive group on the first reactant and the second reactant respectively, the molar ratio of the first reactant and the second reactant used in the first step may be adjusted accordingly. In some embodiments, the amine reactive group on the second reactant may be an Iodine atom, while in other embodiments, the amine reactive group may be a carbonyl chloride group. The first step of the preparation process thus forms an intermediate that may be a combination of one or more molecules of the first reactant with one or more molecules of the second reactant.

In a second step of the preparation process, the intermediate from the first step reacts with a third reactant in the presence of the solvent whereby the secondary amine group on the intermediate reacts with at least one carbonyl chloride group on the third reactant to form at least one amide linkage between the intermediate and the third reactant. Depending upon the number of secondary amine group and the carbonyl chloride group on the intermediate and the third reactant respectively, the amount of the third reactant that is added in the second step may be adjusted accordingly. In the event that the third reactant comprises more than one carbonyl chloride group, the third reactant may be seen as a linker that links multiple intermediate molecules.

At least the structure of one of the first reactant or the second reactant comprises multiple branches. For instance, the first reactant or second reactant may further comprise multiple branching aliphatic groups or optionally substituted aryl groups.

In some embodiments, the structure of the first or the second reactant may not comprise multiple branches. However, the first or the second reactant may comprise multiple functional groups (primary amine groups or amine reactive groups) for attaching a multi branching second or first reactant. As a result, the intermediate formed by the reaction between the first and the second reactant possesses a highly branched structure.

The structure of the third reactant may comprise multiple branches. In some embodiments, the structure of the third reactant does not comprise multiple branches, but the third reactant comprises multiple carbonyl chloride groups. In this case, the third reactant may be seen as a linker that links a multiplicity of branched intermediates to form a hyper-branched compound.

The branches of the hyper-branched compound may be modified to confer desired properties to the hyper-branched compound. More preferably, the branches of the first reactant, second reactant or third reactant may be modified or synthesized with the desired functional groups prior to assembly of the hyper-branched compound.

In some embodiments, the first reactant, the second reactant or the third reactant may comprise branching fluoroalkyl, fluoroaryl or aryl groups substituted with branching fluoroalkyl groups. The resulting hyper-branched compound is highly fluorinated and hence highly hydrophobic.

In other embodiments, the first reactant, the second reactant or the third reactant may be a polyol, with the resulting hyper-branched compound being highly hydrophilic owing to multiple hydroxyl groups.

In one embodiment, the compounds of the present invention are synthesized by first contacting a fluorinated first reactant containing at least one primary amine group with a fluorinated second reactant containing at least one amine reactive group in the presence of a solvent to form a fluorinated intermediate containing at least one secondary amine group. This is followed by contacting the fluorinated intermediate with a third reactant containing at least one carbonyl chloride group to form at least one amide linkage between the fluorinated intermediate and the third reactant to form a fluorinated amide-containing compound comprising n repeat units, wherein n is 1 to 3.

In this embodiment, the first reactant containing at least one primary amine group is a fluorinated aniline. Suitable fluorinated aniline includes 5-bis(triflurormethyl)aniline and 2,4,5-trifluoroaniline. The fluorinated second reactant containing the at least one amine reactive group is heptafluoro-2-iodopropane, with iodine being the amine reactive group. The third reactant containing the at least one carbonyl chloride group can be trimesoyl chloride or 2,4,5-trifluoro-3-methoxybenzoyl chloride.

Figure 9:
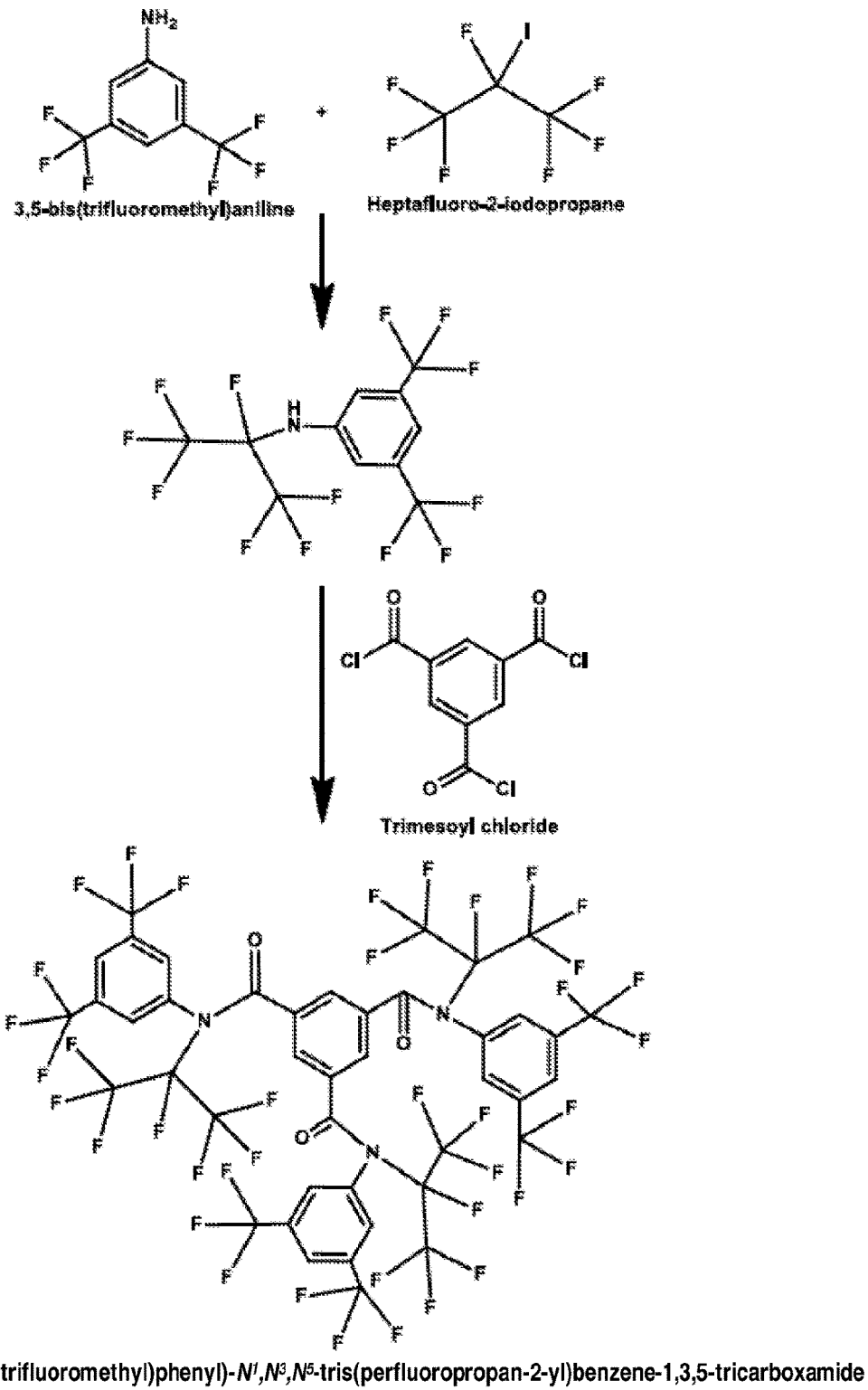
FIG. 9 shows a reaction scheme for preparing a hyper-branched compound in accordance with a third embodiment of the invention.

In one embodiment (as shown in FIG. 9), the first reactant is 3,5-bis(triflurormethyl)aniline, the second reactant is heptafluoro-2-iodopropane, and the third reactant is trimesoyl chloride, forming a fluorinated tertiary amine-containing compound, $N^1,N^3,N^5$-tris(3,5-bis(trifluoromethyl)phenyl)-$N^1,N^3,N^5$-tris(perfluoropropan-2-yl)benzene-1,3,5-tricarboxamide, represented by the structural formula (A).

In another embodiment (as shown in FIG. 1), the first reactant is 2,4,5-trifluoroaniline, the second reactant is heptafluoro-2-iodopropane, and the third reactant is trimesoyl chloride, forming a fluorinated tertiary amine-containing compound $N^1,N^3,N^5$-tris(perfluoropropan-2-yl)-$N^1,N^3,N^5$-tris(2,4,5-trifluorophenyl)benzene-1,3,5-tricarboamide, represented by the structural formula (B).

Figure 5:
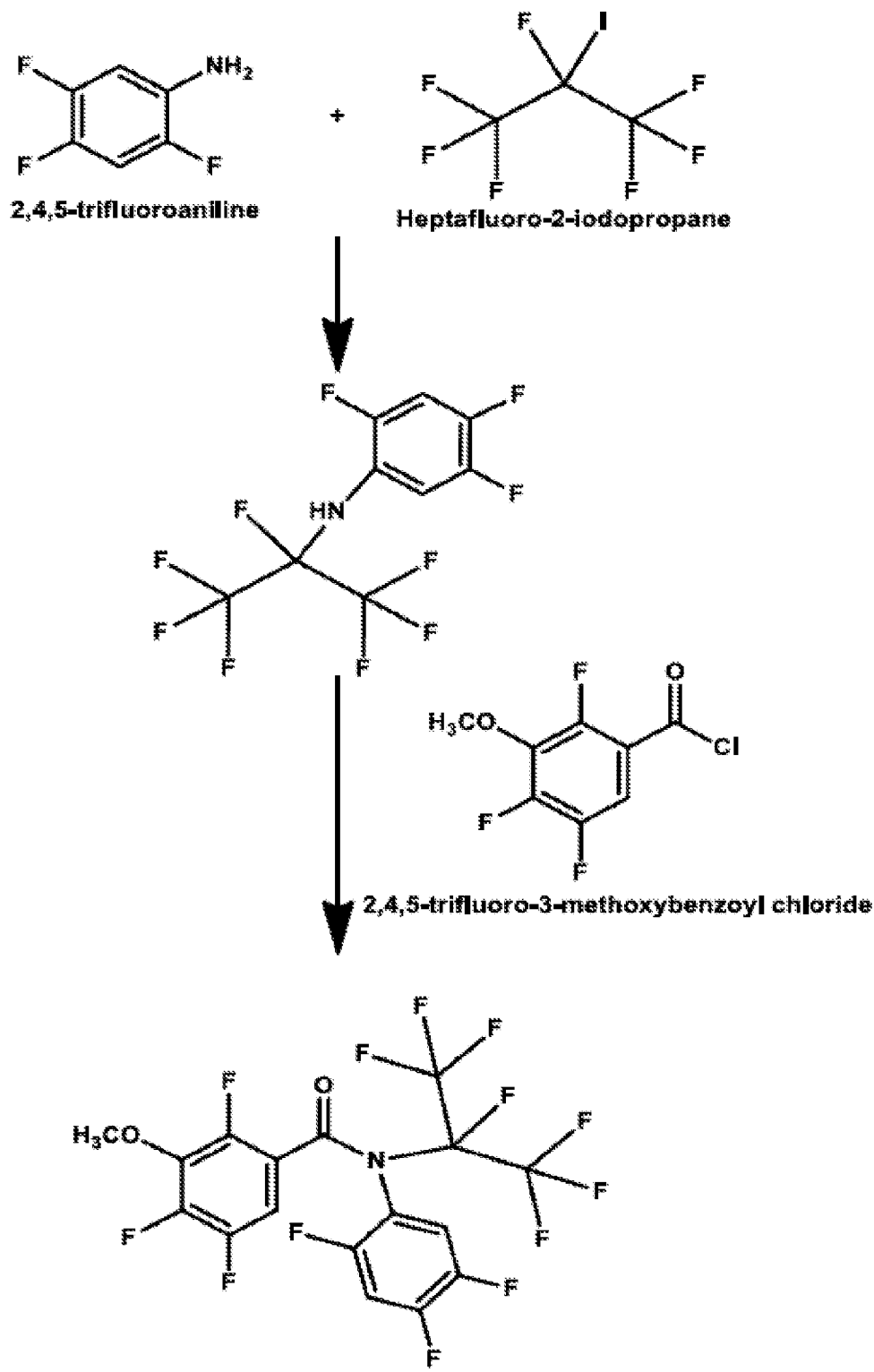
FIG. 5 shows a reaction scheme for preparing a hyper-branched compound in accordance with a second embodiment of the invention.

In yet another embodiment (as shown in FIG. 5), the first reactant is 2,4,5-trifluoroaniline, the second reactant is heptafluoro-2-iodopropane, and the third reactant is 2,4,5-trifluoro-3-methoxybenzoyl chloride, forming a fluorinated tertiary amine-containing compound, 2,4,5-trifluoro-3-methoxy-N-(perfluoropropan-2-yl)-N-(2,4,5-trifluorophenyl) benzamide, represented by the structural formula (C).

In another aspect of the present invention, a hyper-branched compound comprising functionalized graphene is provided. The hyper-branched compound having the following general structure (1):

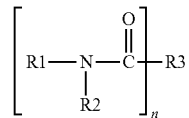

wherein
n denotes an integer representing the number of repeat units and the integer is >1;
R2 is a fluorinated alkyl amine;
R1 is hydrogen; and
R3 is graphene functionalized with n repeat units.

In one embodiment, the fluorinated alkyl amine has the following structure (III):

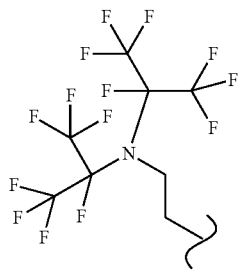
(III)

The hyper-branched compound comprising functionalized graphene is synthesized by contacting a first reactant containing at least one primary amine functionalized graphene with a fluorinated second reactant containing at least one amine reactive group in the presence of a solvent to form at least one amide linkage between the first reactant and the second reactant to form a fluorinated functionalized graphene compound comprising n repeat units, wherein n is >1.

Figure 12:
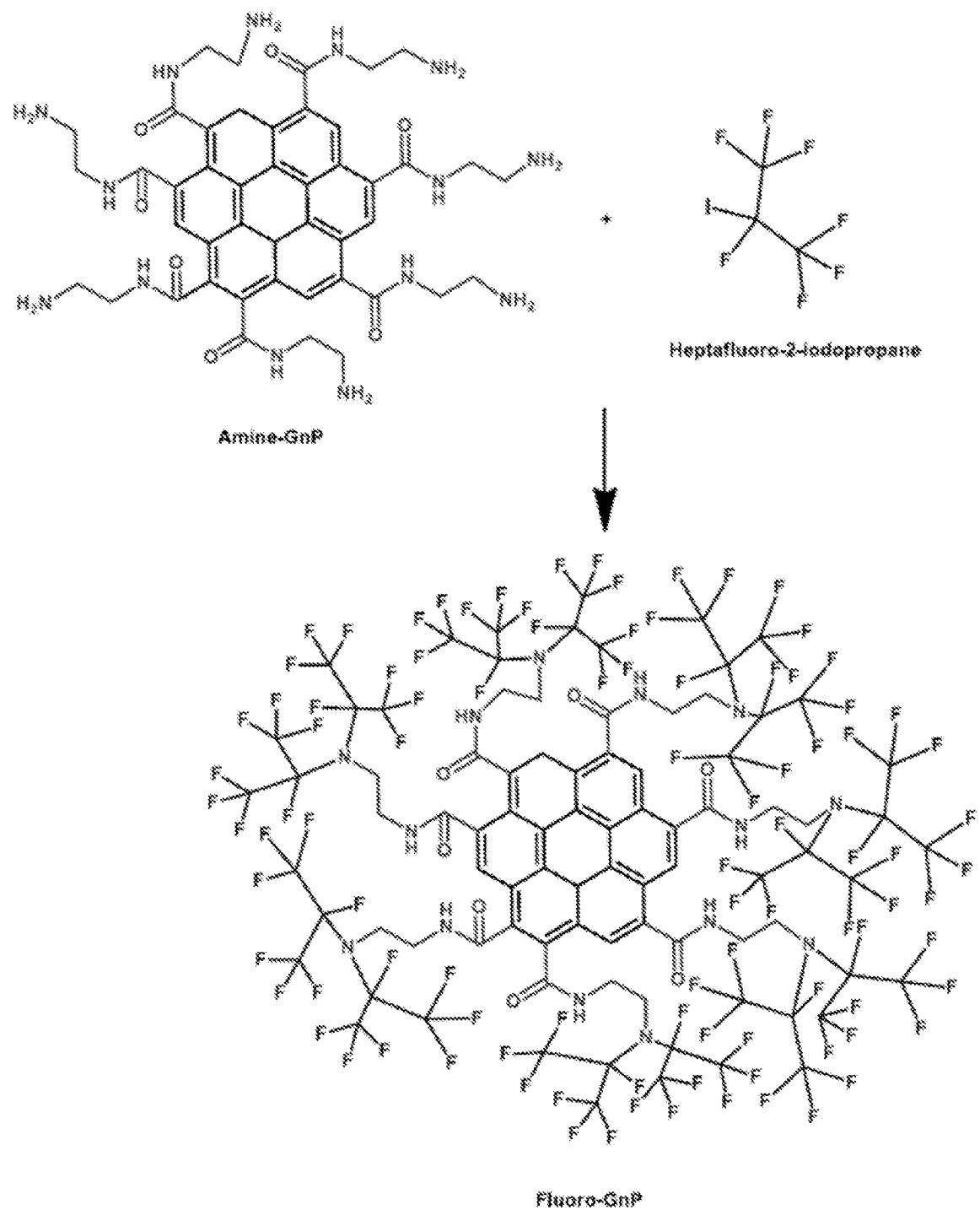
FIG. 12 shows a reaction scheme for preparing a hyper-branched compound in accordance with a fourth embodiment of the invention.

In one embodiment (as shown in FIG. 12), the amine reactive group is iodine. The first reactant is ethylenediamine functionalized graphene having the following structural formula (IV):

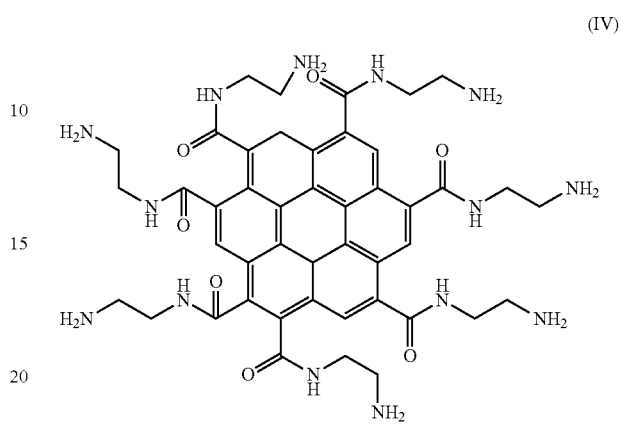
(IV)

The second reactant is heptafluoro-2-iodopropane. The hyper-branched compound comprising fluorinated functionalized graphene has the following structural formula (D):

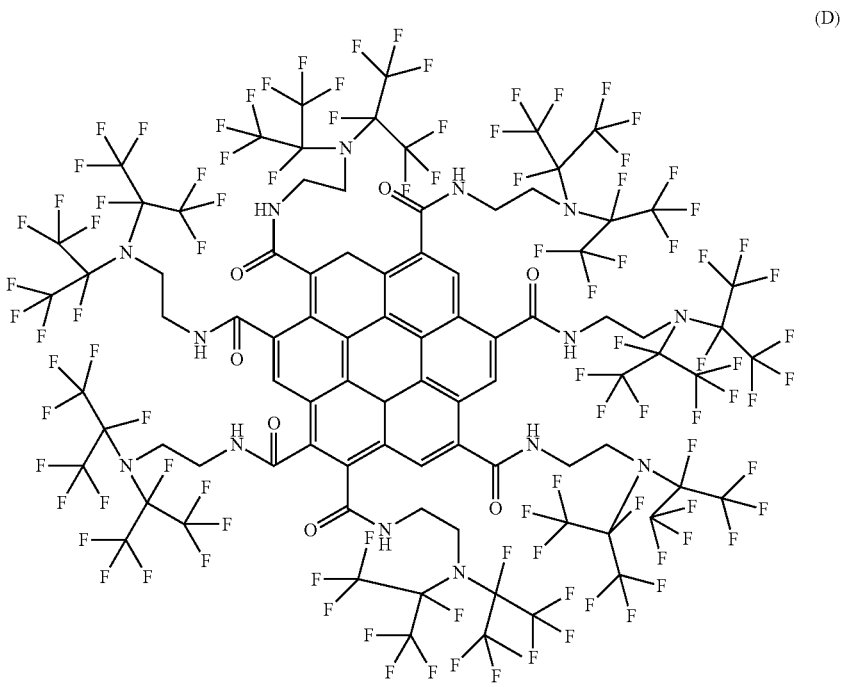 [SMILES: CC(F)(F)C(F)(N(CCNC(=O)C1=C2C=C(C(=O)NCCN(C(F)(C(F)(F)F)C(F)(F)F)C(F)(C(F)(F)F)C(F)(F)F)c3cc(C(=O)NCCN(C(F)(C(F)(F)F)C(F)(F)F)C(F)(C(F)(F)F)C(F)(F)F)c4cc(C(=O)NCCN(C(F)(C(F)(F)F)C(F)(F)F)C(F)(C(F)(F)F)C(F)(F)F)c5c6c4c3C2c2c-6c(c(C(=O)NCCN(C(F)(C(F)(F)F)C(F)(F)F)C(F)(C(F)(F)F)C(F)(F)F)cc2=C1C(=O)NCCN(C(F)(C(F)(F)F)C(F)(F)F)C(F)(C(F)(F)F)C(F)(F)F)=C(C(=O)NCCN(C(F)(C(F)(F)F)C(F)(F)F)C(F)(C(F)(F)F)C(F)(F)F)C5)C(F)(C(F)(F)F)C(F)(F)F)C(F)(F)F]
(D)

The hyper-branched fluorinated compounds of the present invention are highly hydrophobic and thermally stable. The compounds have improved hydrophobic and thermal properties suitable for steam and vapour transportation.

Dependent on the terminal chemical group of the branches of the hyper-branched compounds, the properties of the hyper-branched compounds may be tuned for diverse applications. The branches of the hyper-branched compound may be modified to confer desired properties to the hyper-branched compound. More preferably, the branches of the first reactant, second reactant or third reactant may be modified or synthesized with the desired functional groups prior to assembly of the hyper-branched compound.

For example, in another embodiment of the present invention, a hyper-branched compound comprising functionalized graphene oxide is provided. The hyper-branched compound has the same general structure (I):

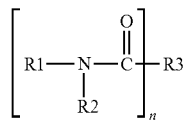

(I)

wherein
R1 is a hydrogen;
R2 is a tertiary amine having the following structure (V):

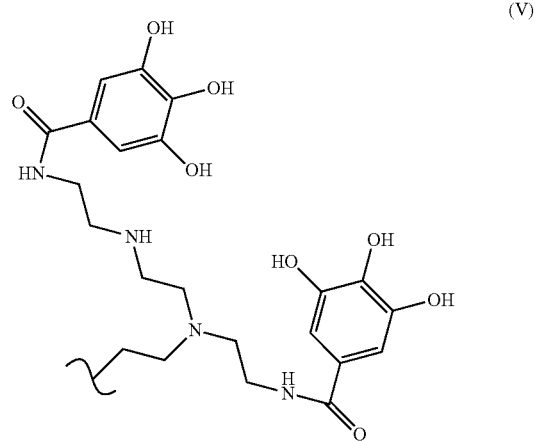 [SMILES: CCCN(CCNCCNC(=O)c1cc(O)c(O)c(O)c1)CCNC(=O)c1cc(O)c(O)c(O)c1]

(V)

and R3 is a graphene oxide functionalized with n repeat units. The hyper-branched compound of this embodiment has the following structural formula (E):

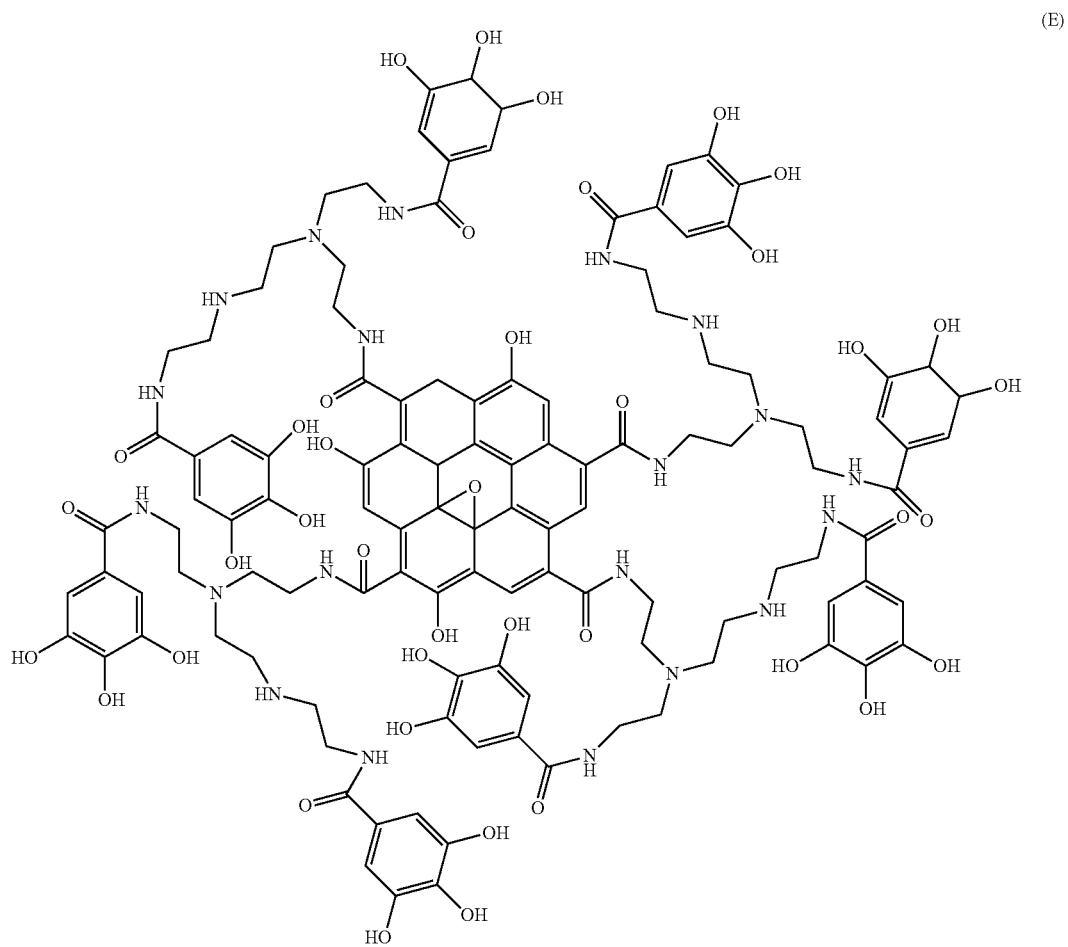

(E)

The hyper-branched compound of structural formula (E) is synthesized by contacting a first reactant containing at least one primary amine group with a second reactant containing at least one amine reactive group in the presence of a solvent to form an intermediate; and contacting the intermediate with a third reactant containing at least one carbonyl chloride group to form at least one amide linkage between the intermediate and the third reactant to form an amine functionalized graphene oxide compound comprising n repeat units, wherein n is >1.

Figure 13:
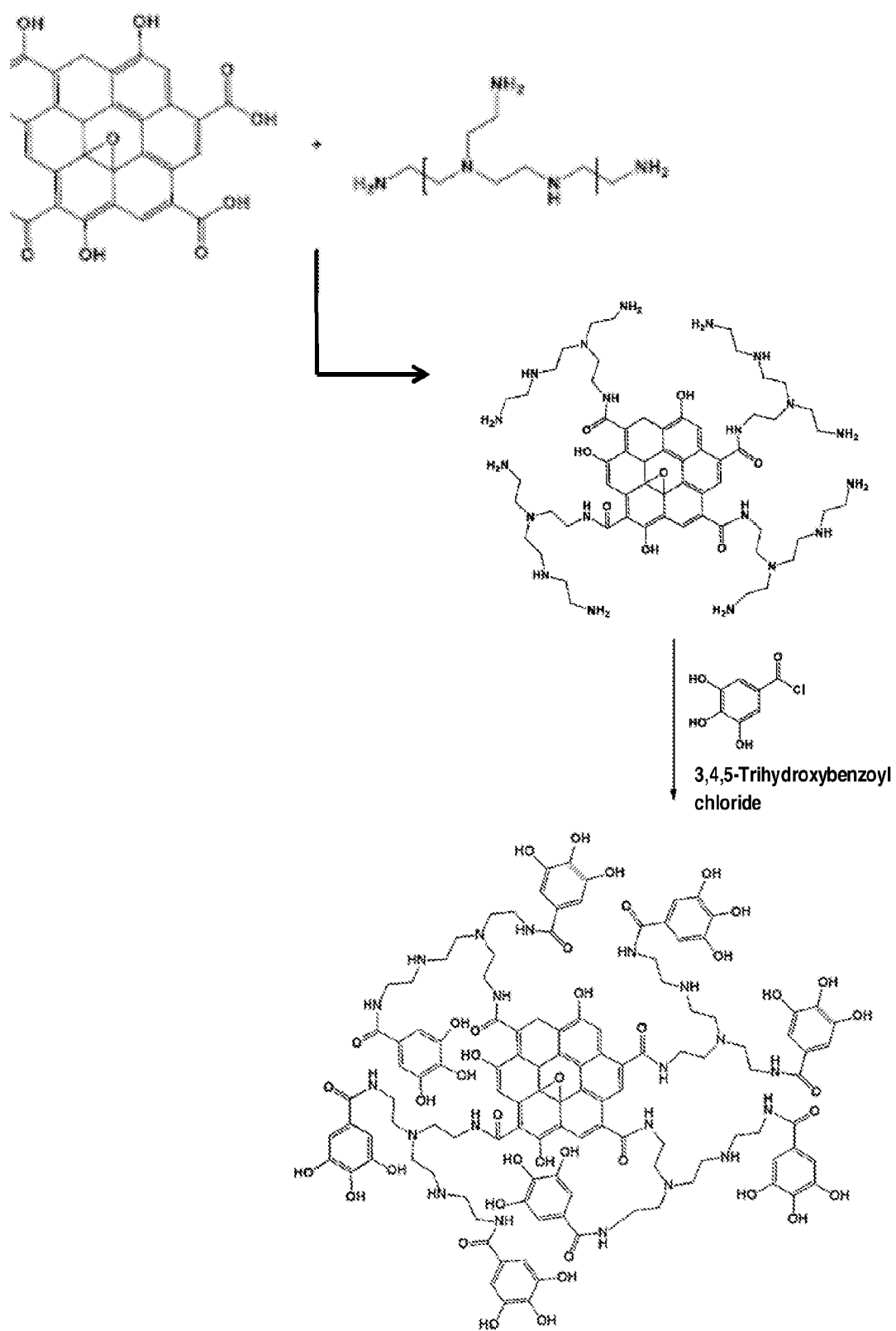
FIG. 13 shows a reaction scheme for preparing a hyper-branched compound in accordance with a fifth embodiment of the invention.

In one embodiment (as shown in FIG. 13), the first reactant is a hyper-branched polyethyleneimine, the second reactant is a carboxylic group functionalized graphene oxide and the third reactant is 3,4,5-trihydroxybenzoyl chloride. The amine reactive group from the second reactant is the —OH from the carboxylic group of the graphene oxide.

The hyper-branched compound of this embodiment, which comprises amine functionalized graphene oxide, is highly hydrophilic owing to the multiple hydroxyl groups present in the compound.

Preferably, the hyper-branched compounds of the present invention are synthesized under the conditions of constant stirring of the solution comprising an appropriate amount of the first reactant and the second reactant in the presence of a solvent, at a temperature of between 50° C. and 70° C. for 1 to 2 hours.

More preferably, first reaction is carried out by stirring continuously a solution comprising an appropriate amount of the first reactant and second reactant dissolved in a solvent at a temperature between 50° C. and 70° C. for 1 to 2 hours. Thereafter, an appropriate amount of the third reactant is added to the solution while stirring continuously at a temperature between 50° C. and 70° C. for another 0.25 to 0.5 hour to obtain the hyper-branched compound.

In some embodiments, the solvent used in the methods is dimethylacetamide (DMAc).

Applications of the Hyper-Branched Compounds

Figure 14:
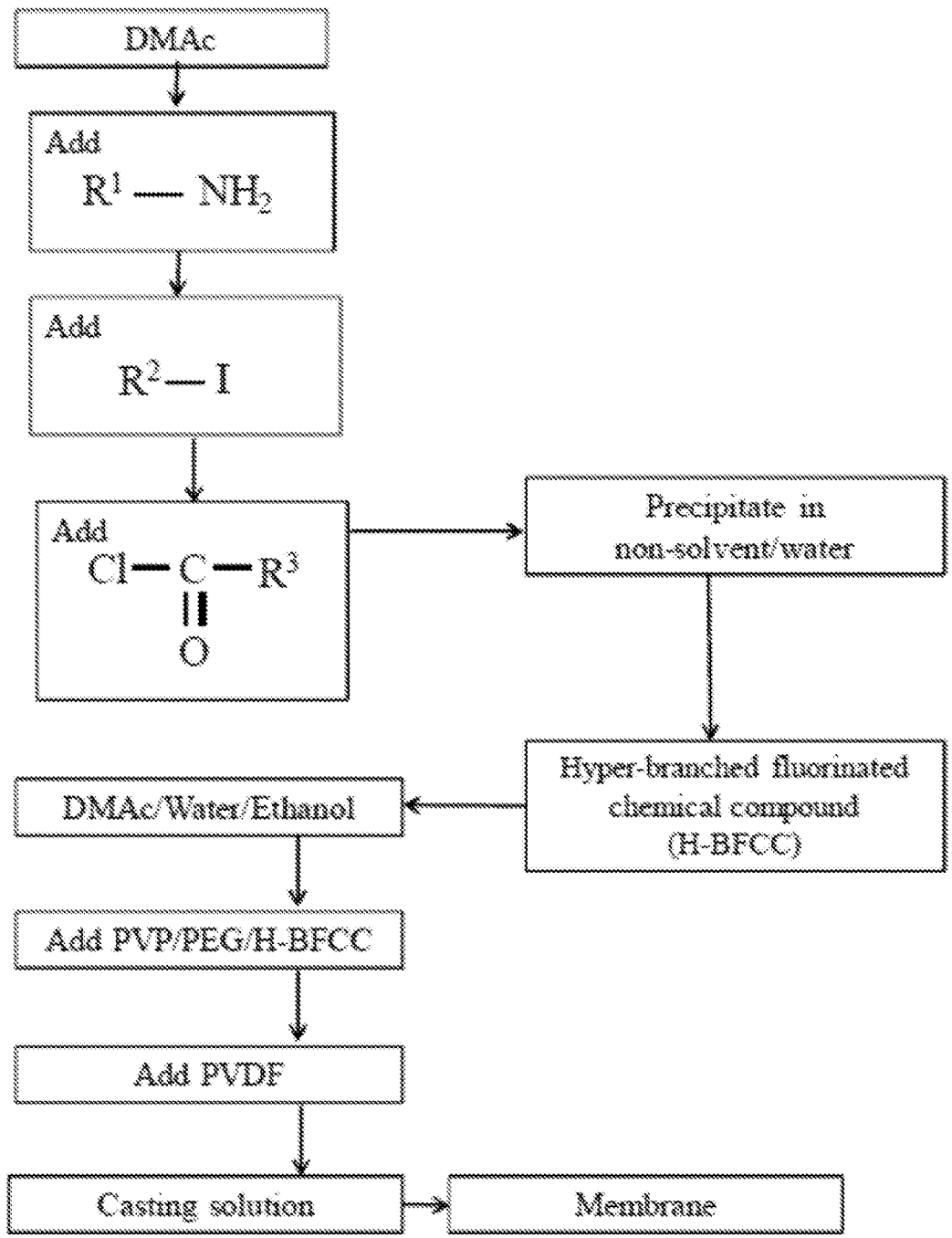
FIG. 14 shows a flow diagram for preparation of a membrane incorporating the hyper-branched chemical compound of the present invention.

In another aspect of the present invention, the hyper-branched compound may be used in diverse applications in various forms. For instance, the hyper-branched compound may be used as additives to alter water affinity of membrane or as hydrophobic coatings, etc. The hyper-branched fluorinated chemical compound (H-BFCC) of the present invention may be used to prepare a casting solution for fabricating hydrophobic membranes or for other purposes. Hydrophobic membranes are resistant to wetting and would be useful for MD as described hereinabove. FIG. 14 outlines a method for fabricating membranes incorporating the H-BFCC of the present invention. The H-BFCC is first synthesized according to the method described herein.

In one aspect of the present invention, a method of preparing a casting solution comprising a hyper-branched compound is provided. The method comprises (a) adding a first reactant to a solvent to obtain a solution, wherein the first reactant comprises at least one primary amine group; (b) adding a second reactant to the solution, wherein the second reactant comprises at least one amine reactive group to form an intermediate comprising at least one secondary amine group; (c) adding a third reactant to the solution, wherein the third reactant comprises at least one carbonyl chloride group to form at least one amide linkage between the intermediate and the third reactant to form a hyper-branched compound with n repeat units, wherein n is 1 to 3 or >1; and (d) adding a base polymer to the solution to form a casting solution.

The first reactant is selected from the group consisting of 3, 5-bis(trifluoromethyl)aniline, 2, 4, 5-trifluoroaniline and hyper-branched polyethyleneimine.

The second reactant is selected from the group consisting of heptafluoro-2-iodopropane and graphene oxide.

The third reactant is selected from the group consisting of trimesoyl chloride, 2,4,5-trifluoro-3-methoxybenzoyl chloride and 3,4,5-trihydroxybenzoyl chloride.

In one embodiment, before adding a base polymer to the solution to form a casting solution, the H-BFCC synthesized from the method is isolated by precipitation in a non-solvent. The H-BFCC is washed and dried prior to dissolving in a suitable solvent, for example DMAc, water and ethanol. Preferably, the H-BFCC is dissolved by continuously stirring the solution using a stirrer (set at 200-300 rpm) at a temperature between 50 to 70° C. for 0.5 to 1 hr.

In some embodiments, additives comprising pore forming agents are added to the solution. Examples of pore forming agents include, but are not limited to, polyvinylpyrrolidone (PVP) and polyethylene glycol (PEG). Preferably, the solution is further stirred at a speed of 200 to 300 rpm at a temperature between 50 to 70° C. for another 0.5 to 1 hr.

Base polymer that forms bulk of the membrane is added to the solution. Suitable base polymer includes, but is not limited to, polyvinylidene fluoride (PVDF). Preferably, the solution is further stirred using a stirrer at a speed of 200 to 300 rpm) at a temperature between 50 to 70° C. for 8 to 12 hr.

As would be understood by the skilled person, the sequence of dissolving the various components may be varied or the components may be simultaneously added to the solvent. The resulting solution is used as a casting solution for fabricating the hydrophobic membranes via techniques known in the common art such as phase inversion method.

Figure 15:
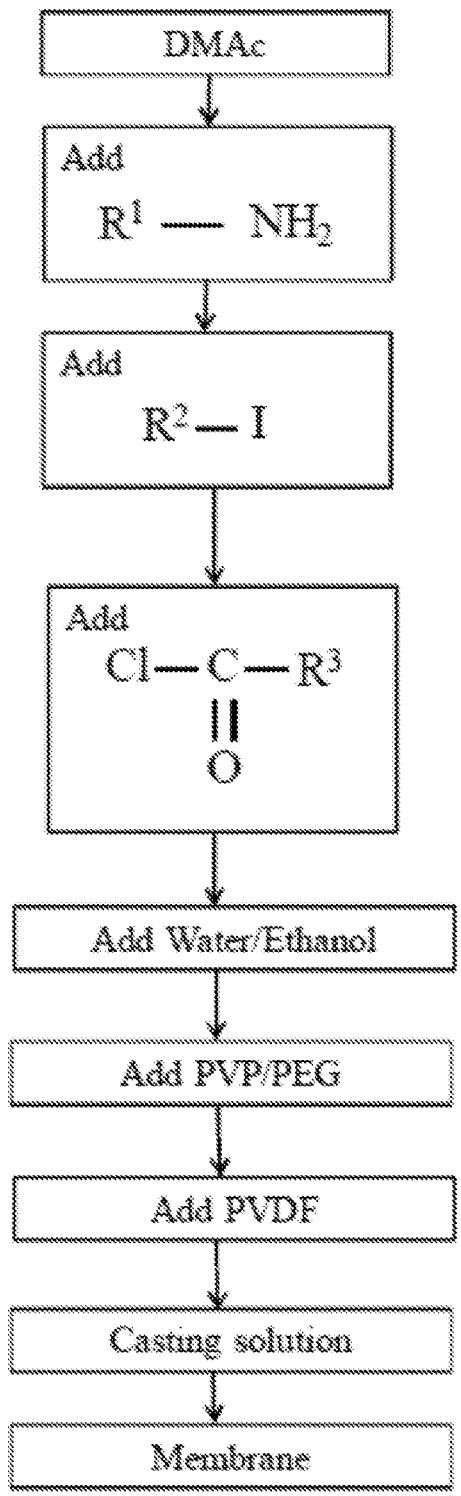
FIG. 15 shows a flow diagram for one-pot preparation of a membrane incorporating the hyper-branched chemical compound of the present invention.

In another embodiment, the H-BFCC and the membrane casting solution are prepared using a one-pot process. As shown in FIG. 15, the H-BFCC is first prepared in a reaction vessel according to the method as described hereinabove. The membrane base polymer such as PVDF, other optional additives (for example, PVP, PEG), and non-solvent such as ethanol-water are then added to the same reaction vessel for preparing the casting solution.

The present inventor has found that the method for preparing a hyper-branched compound as described herein provides a good yield and relative ease in preparation by using moderate temperature and common solvent. Hyper-branched compound with good thermal stability may be obtained by choosing reactants with aryl groups. The method may be seamlessly incorporated into preparation of a membrane casting solution that is used to fabricate membrane, for use in membrane distillation process or other downstream processes. The invention is further explained by way of examples.

EXAMPLES

Example 1: Synthesis of $N^1,N^3,N^5$-tris(perfluoropropan-2-yl)-$N^1,N^3,N^5$-tris(2,4,5-trifluorophenyl) benzene-1,3,5-tricarboamide 2,4,5-trifluoroaniline and heptafluoro-2-iodopropane in 1:1 molar ratio were dissolved in 20 ml of DMAc and allowed to stir at a temperature of 80° C. for 1-2 hours. After two hours, trimesoyl chloride (TMC) was added to the solution. The ratio of TMC to the intermediate secondary amine was calculated to be 1:3. The solution was stirred under controlled temperature of 80° C. for another 20-30 mins. The final dark brown solution was poured into crushed ice/cool water slowly to get a yellowish brown precipitate of N¹,N³,N⁵-tris(perfluoropropan-2-yl)-N¹,N³,N⁵-tris(2,4,5-trifluorophenyl)benzene-1,3,5-tricarboamide (see FIG. 1). The product was filtered, washed with water and dried in vacuum oven before characterization.

Structure Confirmation

Figure 2:
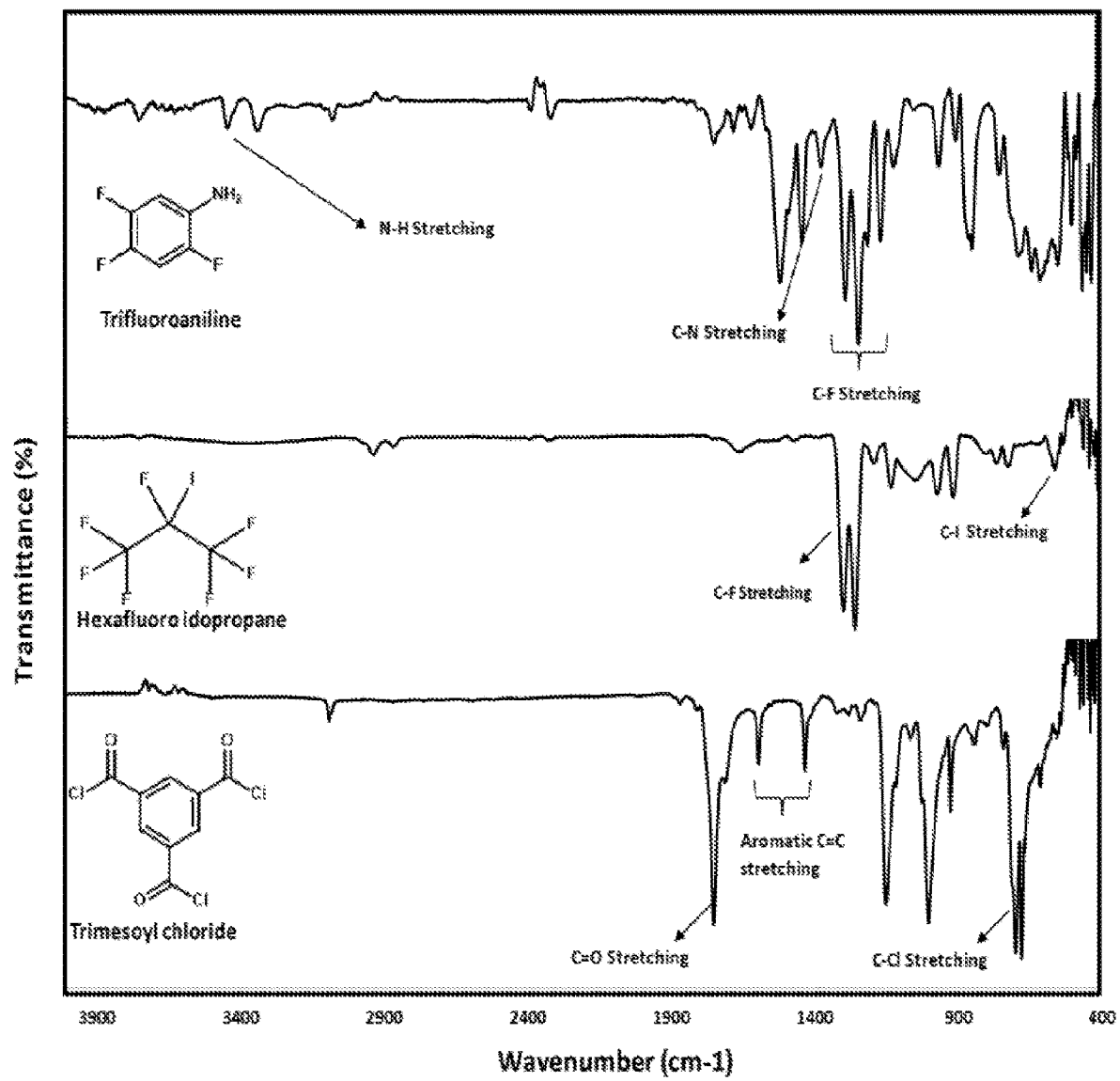
FIG. 2 is a FTIR spectra of the reactants used in Example 1 for the preparation of the hyper-branched compound of FIG. 1.

The structure of N¹,N³,N⁵-tris(perfluoropropan-2-yl)-N¹,N³,N⁵-tris(2,4,5-trifluorophenyl)benzene-1,3,5-tricarboamide was confirmed by Fourier Transform Infra-Red (FTIR) spectroscopy. FIG. 2 shows the FTIR spectra of 2,4,5-trifluoroaniline, heptafluoro-2-iodopropane and trimesoyl chloride. In the spectrum of 2,4,5-trifluoroaniline, the small broad stretch around 3343 cm$^{-1}$ corresponds to N—H stretching vibration. A small peak at 1367 cm$^{-1}$ corresponds to C—N stretching vibration and C—F stretching vibrations were observed around 1280 cm$^{-1}$. Similarly, the FTIR spectrum of heptafluoro-2-iodopropane shows strong peaks at 1200 cm$^{-1}$ corresponding to C—F stretching vibration and a small peak at 530 cm$^{-1}$ for C—I. The FTIR spectrum for trimesoyl chloride shows characteristic peaks at 1749 cm$^{-1}$, 690 cm$^{-1}$ and 1400-1500 cm$^{-1}$ for C=O stretching, C—Cl stretching and C=C stretching vibrations respectively.

Figure 3:
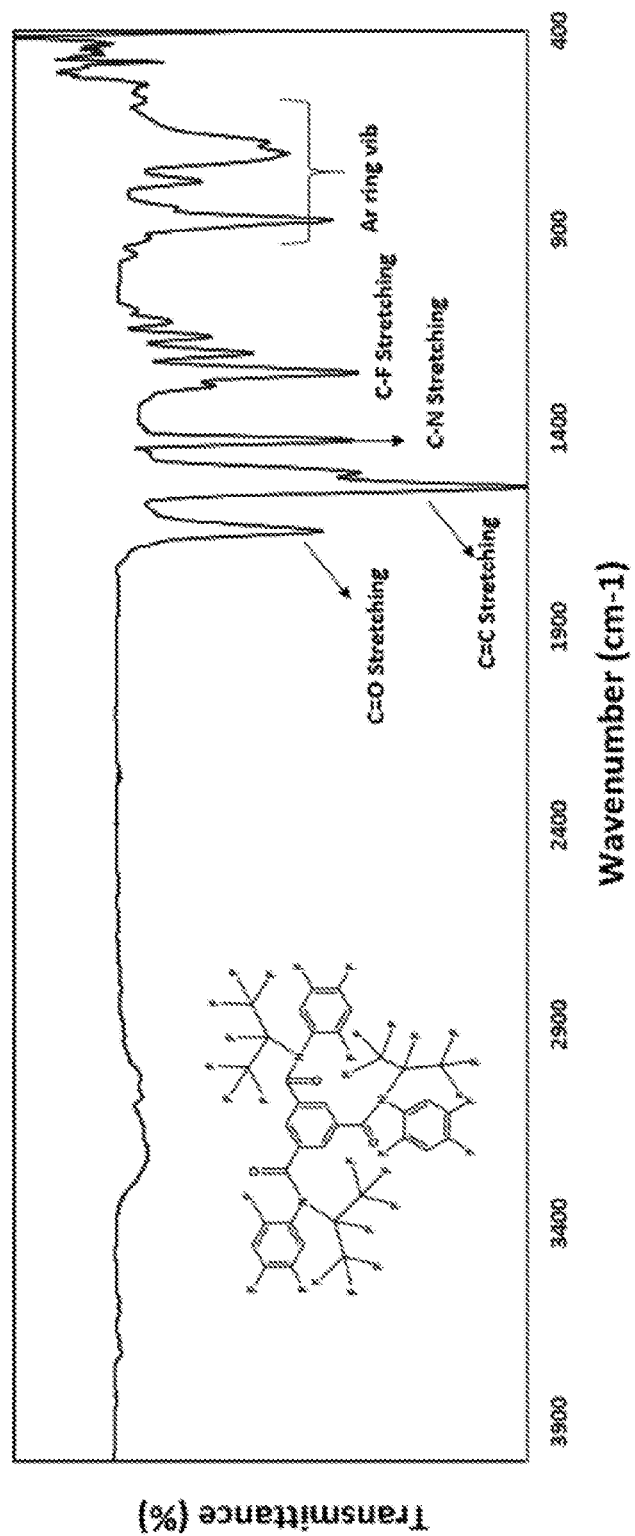
FIG. 3 is a FTIR spectrum of the hyper-branched compound of FIG. 1, produced in Example 1.

FIG. 3 shows the FTIR spectra of the final product, N¹,N³,N⁵-tris(perfluoropropan-2-yl)-N¹,N³,N⁵-tris(2,4,5-trifluorophenyl)benzene-1,3,5-tricarboamide. The FT IR spectrum shows a small peak at 3062 cm$^{-1}$ for C—H stretching vibration, a sharp peak at 1658 cm$^{-1}$ for C=O stretching vibration, another peak at 1429 cm$^{-1}$ for C—N stretching vibration and finally a peak at 1257 cm$^{-1}$ for C—F stretching vibration, hence confirming formation of the product. The ring deformation and C=C vibrations were also observed.

Thermal Stability

Figure 4:
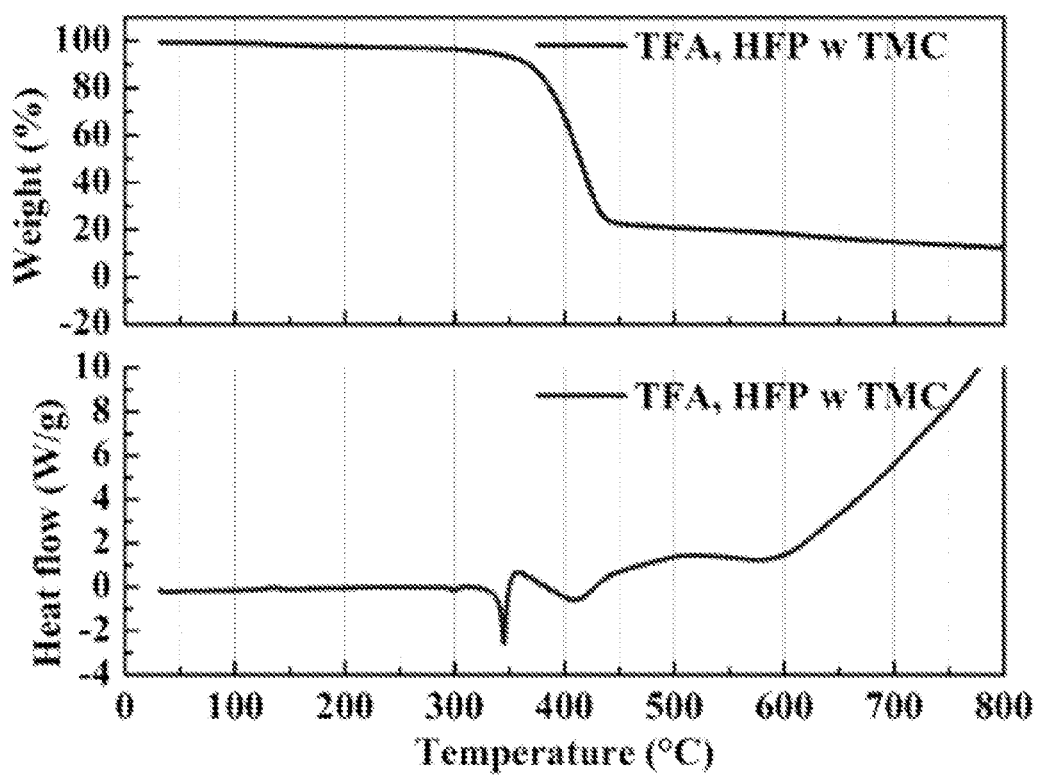
FIG. 4 shows the TGA data of the hyper-branched compound of FIG. 1, produced in Example 1.

The thermal stability of N¹,N³,N⁵-tris(perfluoropropan-2-yl)-N¹,N³,N⁵-tris(2,4,5-trifluorophenyl)benzene-1,3,5-tricarboamide was analyzed by thermo gravimetric analysis (TGA). The results, as shown in FIG. 4, confirms formation of a high molecular weight product which has a single stage decomposition with a high initial decomposition of about 350° C. The decomposition ends at around 425° C.

Example 2: Synthesis of 2,4,5-trifluoro-3-methoxy-N-(perfluoropropan-2-yl)-N-(2,4,5-trifluorophenyl) benzamide 2,4,5-trifluoroaniline and heptafluoro-2-iodopropane in 1:1 molar ratio were dissolved in 20 ml of DMAc and allowed to stir at a temperature of 80° C. for 1-2 hours. After two hours, 2,4,5-trifluoro-3-methoxybenzoyl chloride (TFMBC) was then added to the solution. The ratio of TFMBC to the intermediate secondary amine was calculated to be 1:1. The solution was stirred under controlled temperature of 80° C. for another 20-30 mins. The final yellow solution was poured into crushed ice/cool water slowly to get a pale yellowish precipitate of 2,4,5-trifluoro-3-methoxy-N-(perfluoropropan-2-yl)-N-(2,4,5-trifluorophenyl) benzamide (see FIG. 5). The product was filtered, washed with water and dried in vacuum oven before characterization.

Structure Confirmation

Figure 6:
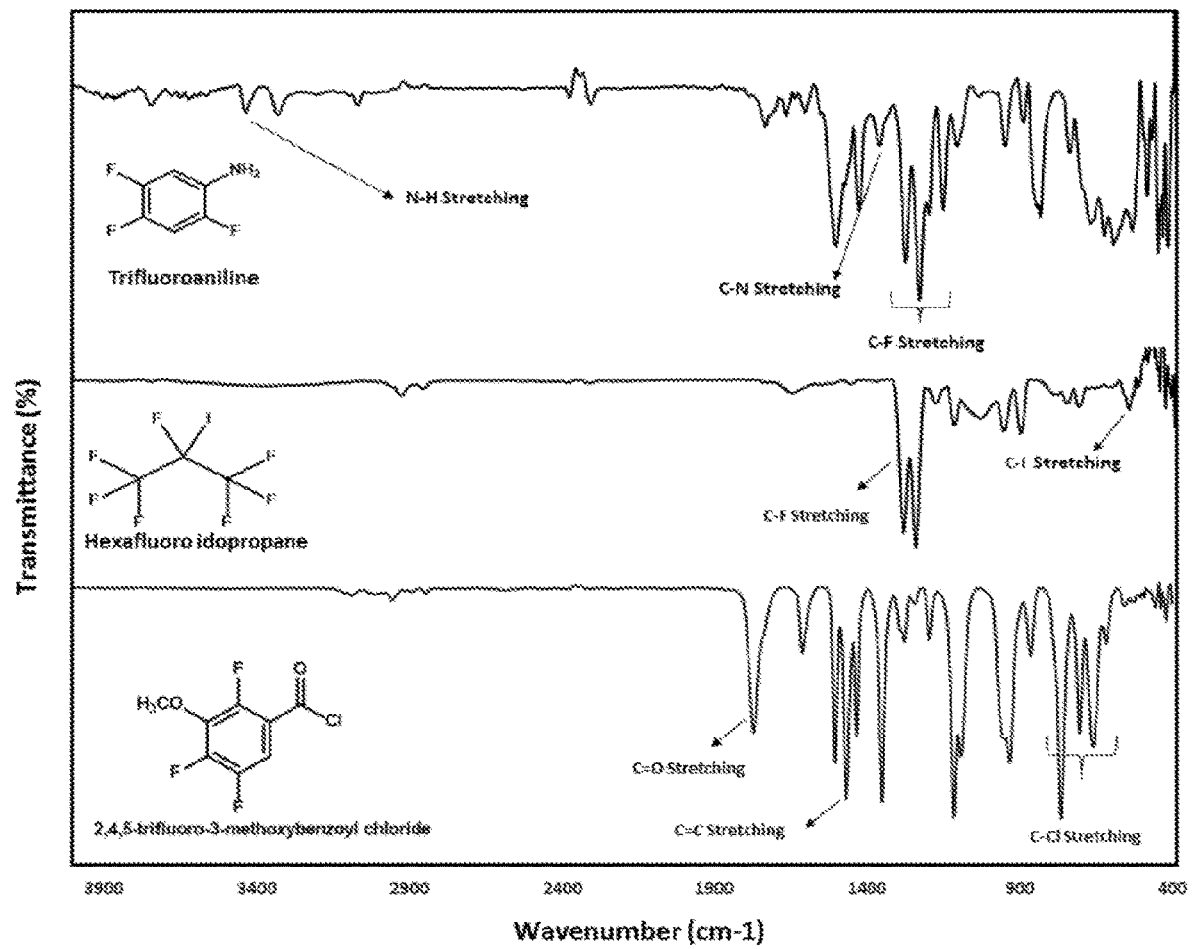
FIG. 6 is a FTIR spectra of the reactants used in Example 2 for the preparation of the hyper-branched compound of FIG. 5.

The structure of 2,4,5-trifluoro-3-methoxy-N-(perfluoropropan-2-yl)-N-(2,4,5-trifluorophenyl) benzamide was confirmed by FTIR spectroscopy. FIG. 6 shows the FTIR spectra of 2,4,5-trifluoroaniline, heptafluoro-2-iodopropane and TFMBC. The FTIR spectrum of 2,4,5-trifluoroaniline shows a small broad stretch around 3343 cm$^{-1}$ corresponding to N—H stretching vibration. A small peak at 1367 cm$^{-1}$ corresponds to the C—N stretching vibration and C—F stretching vibrations were observed around 1280 cm$^{-1}$. The FTIR spectrum of heptafluoro-2-iodopropane shows strong peaks at 1200 cm$^{-1}$ for C—F stretching vibration and a small peak at 530 cm$^{-1}$ for C—I. The FTIR for TFMBC shows characteristic peaks at 1770 cm$^{-1}$, 763-649 cm$^{-1}$ and 1400-1500 cm$^{-1}$ for C=O stretching, C—Cl stretching and C=C stretching vibrations respectively.

Figure 7:
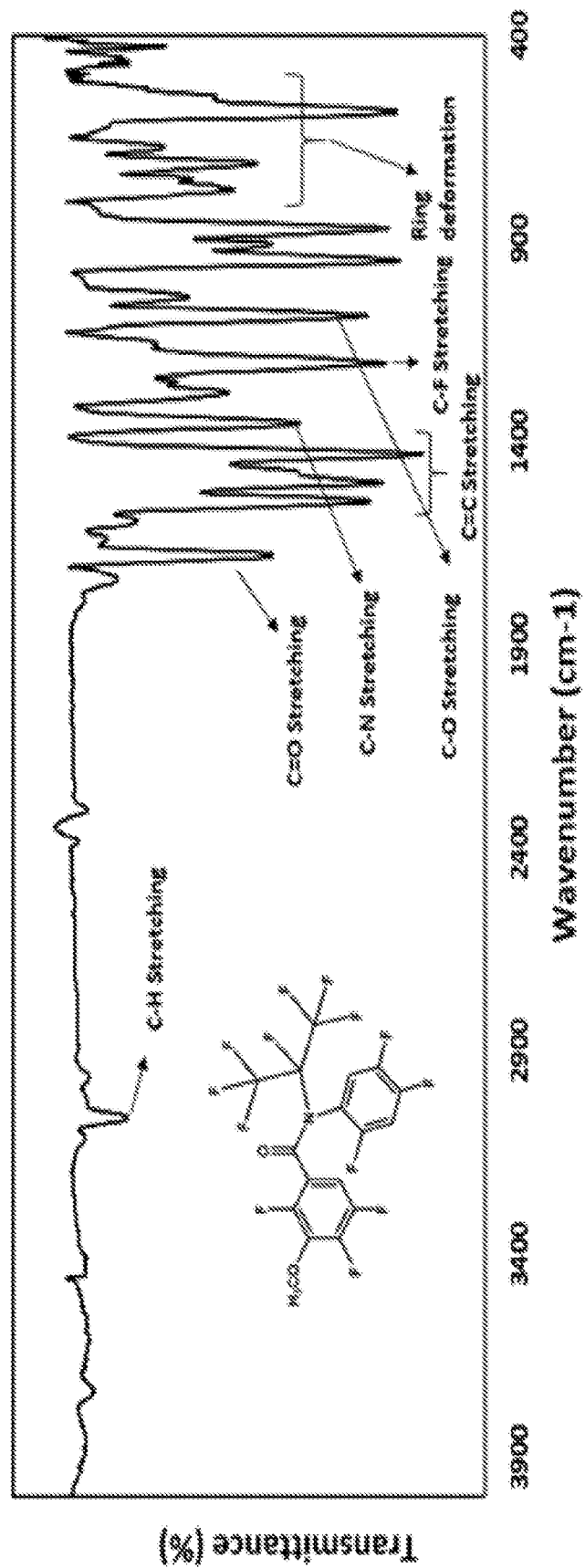
FIG. 7 is a FTIR spectrum of the hyper-branched compound of FIG. 5, produced in Example 2.

FIG. 7 shows the FTIR spectrum of the final product 2,4,5-trifluoro-3-methoxy-N-(perfluoropropan-2-yl)-N-(2,4,5-trifluorophenyl) benzamide. The FTIR spectrum shows a small_peak at 3062 cm$^{-1}$ for C—H stretching vibration, a sharp peak at 1682 cm$^{-1}$ for C=O stretching vibration, another peak at 1355 cm$^{-1}$ for C—N stretching vibration, 1089 cm$^{-1}$ for C—O stretching vibration and finally a peak at 1207-1280 cm$^{-1}$ for C—F stretching vibration, hence confirming formation of the product. The ring deformation and C=C vibration a were also observed.

Thermal Stability

Figure 8:
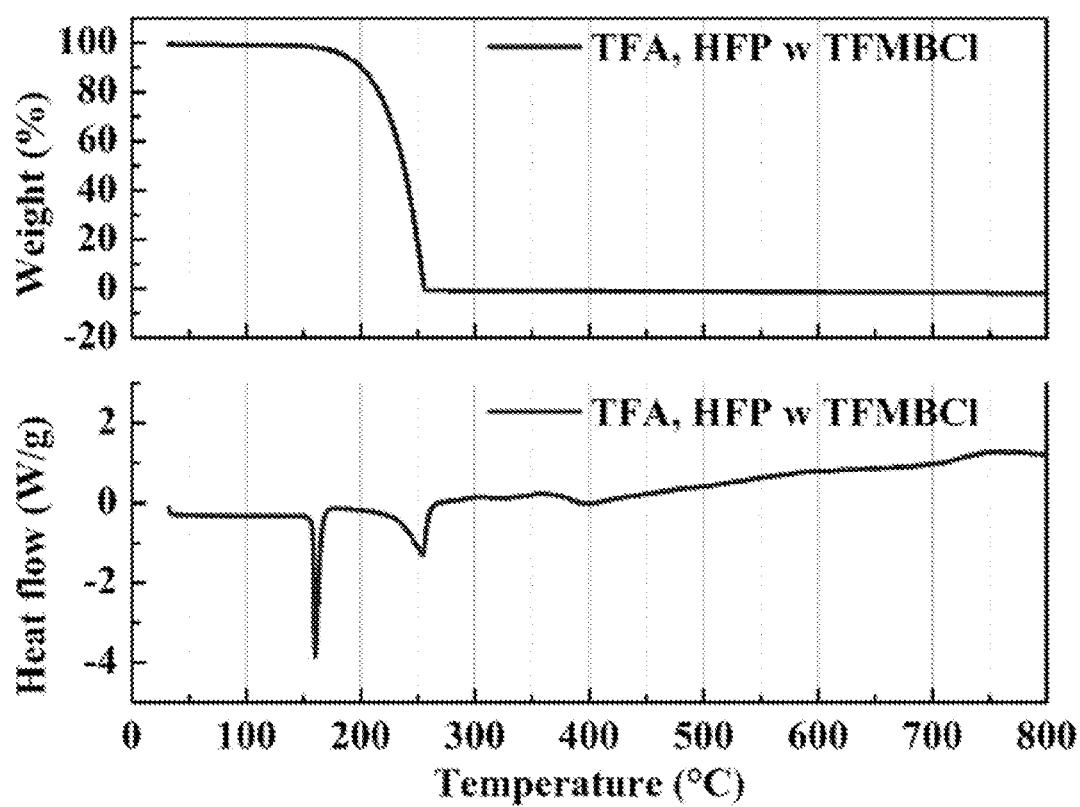
FIG. 8 shows the TGA data of the hyper-branched compound of FIG. 5, produced in Example 2.

The thermal stability of 2,4,5-trifluoro-3-methoxy-N-(perfluoropropan-2-yl)-N-(2,4,5-trifluorophenyl) benzamide was analyzed by TGA. The results, as shown in FIG. 8, confirm formation of a medium molecular weight product which has single stage decomposition with decomposition starting at 200° C. The decomposition ends at around 250° C.

Example 3: Synthesis of N¹,N³,N⁵-tris(3,5-bis(trifluoromethyl)phenyl)-N¹,N³,N⁵-tris(perfluoropropan-2-yl)benzene-1,3,5-tricarboxamide 3,5-bis(trifluoromethyl)aniline and heptafluoro-2-iodopropane in 1:1 molar ratio were dissolved in 20 ml of DMAc and allowed to stir at a temperature of 80° C. for 1-2 hours. After two hours, trimesoyl chloride (TMC) was then added to the solution. The ratio of TMC to the intermediate secondary amine was calculated to be 1:3. The solution was stirred under controlled temperature of 80° C. for another 20-30 mins. The final solution was poured into crushed ice/cool water slowly to get a precipitate of N¹,N³,N⁵-tris(3,5-bis(trifluoromethyl)phenyl)-N¹,N³,N⁵-tris(perfluoropropan-2-yl)benzene-1,3,5-tricarboxamide (see FIG. 9). The product was filtered, washed with water and dried in vacuum oven before characterization.

Structure Confirmation

Figure 10:
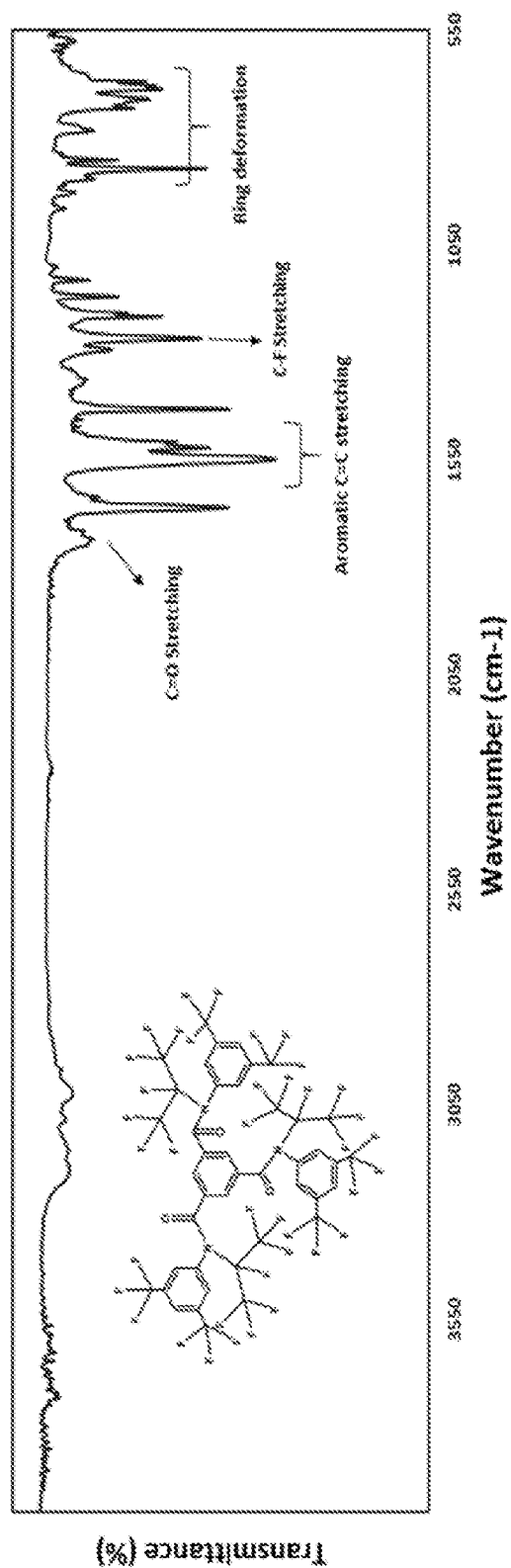
FIG. 10 is a FTIR spectrum of the hyper-branched compound of FIG. 9, produced in Example 3.

FIG. 10 shows the FTIR spectrum of the final product, N¹,N³,N⁵-tris(3,5-bis(trifluoromethyl)phenyl)-N¹,N³,N⁵-tris(perfluoropropan-2-yl)benzene-1,3,5-tricarboxamide. The FTIR spectrum shows a small peak around 1734 cm$^{-1}$ for C=O stretching vibration, a sharp peaks around 1660 to 1430 cm$^{-1}$ for C=C stretching vibration, another peak at 680 cm$^{-1}$ for CF stretching vibration, hence confirming formation of the product. The ring deformation vibrations were also observed.

Thermal Stability

Figure 11:
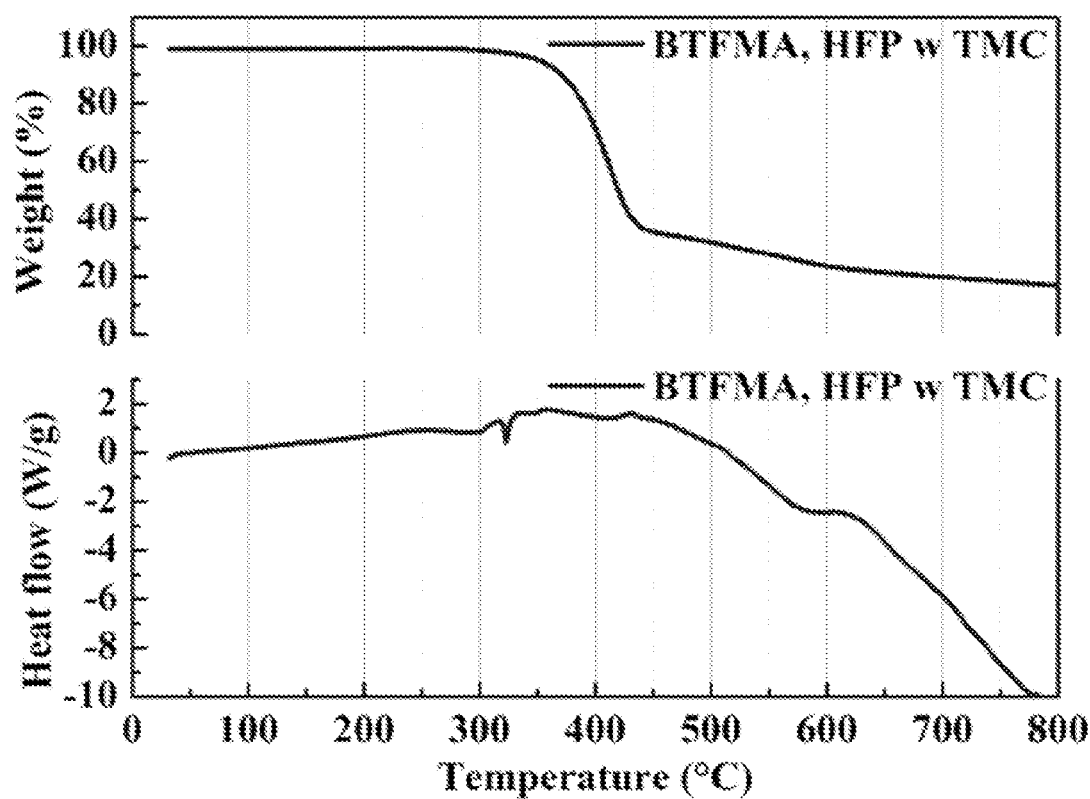
FIG. 11 shows the TGA data of the hyper-branched compound of FIG. 9, produced in Example 3.

The thermal stability of N¹,N³,N⁵-tris(3,5-bis(trifluoromethyl)phenyl)-N¹,N³,N⁵-tris(perfluoropropan-2-yl)benzene-1,3,5-tricarboxamide was analyzed by TGA. The results, as shown in FIG. 11, confirms formation of a medium weight product which has single stage decomposition with decomposition starting at 350° C. The decomposition ends at around 420° C.

Example 4: Development of Highly Hydrophobic, Thermally Stable and Hyper-Branched Fluorinated Chemical Compound-Based Flat Sheet Membrane for Steam and Vapour Transportation The highly hydrophobic, thermally stable and hyper-branched fluorinated compound-based flat sheet membrane was fabricated by the conventional phase inversion method. The casting solution used in the phase inversion method was prepared by dissolving PVDF in DMAc/ethanol solvent mixture and PVP was used as pore former.

The highly hydrophobic, thermally stable, hyperbranched chemical compound (H-BFCC) as synthesized by the preceding examples was added to improve hydrophobicity of the membrane. The compositions of the casting solutions are given in Table 1 below.

The PVDF polymer and PVP additive were added into the mixed solvent (DMAc/Ethanol) in a RB flask and stirred at 200~300 rpm for at least 12-18 h at 60-80° C. to make a homogeneous casting solution. The casting solution was then casted onto a glass plate using a casting plate with thickness 100 μm, before being subjected to the non-solvent (water) bath for precipitation process. The casted membrane was soaked in a water bath overnight and rinsed with water to remove the solvent. Following the rinsing process, the membranes were subjected to a post treatment process whereby the membranes were washed with water, ethanol and hexane to remove hydrophilic substance and additives from the membrane matrix/surface. The post-treated membranes were dried at room temperature for 24 hrs.

TABLE 1

Compositions of the casting solutions

| Sample ID | PVDF-Kynar-761 (wt %) | PVP-K30 (wt %) | H-BFCC (wt %) | DMAC (wt %) | Ethanol (wt %) |
|---|---|---|---|---|---|
| M1 | 21 | 10 | 0 | 67 | 2 |
| M2 | 21 | 10 | 1 | 66 | 2 |
| M3 | 21 | 10 | 3 | 64 | 2 |
| M4 | 21 | 10 | 5 | 62 | 2 |
| M5 | 21 | 10 | 7 | 60 | 2 |

The prepared membranes were characterized in terms of thickness, pore size, liquid entry pressure (LEPw) and water contact angle (CAw) and the results are presented in the Table 2 below.

TABLE 2

Membrane characterisation data

| Membrane ID | Thickness (μm) | Pore size (μm) | LEPw (kPa) | CAw (°) |
|---|---|---|---|---|
| M1 | 100 ± 10 | 0.14 ± 0.02 | 200 ± 10 | 91.6 ± 2.1 |
| M2 | 100 ± 10 | 0.14 ± 0.02 | 280 ± 30 | 97.4 ± 3.0 |
| M3 | 100 ± 10 | 0.13 ± 0.02 | 350 ± 20 | 112.3 ± 4.1 |
| M4 | 100 ± 10 | 0.13 ± 0.03 | 380 ± 20 | 117.5 ± 3.6 |
| M5 | 100 ± 10 | NA | 7 | 123.2 ± 3.1 |

From the experimental data, it can be identified that there is not much differences in membrane thickness and pore size between membranes fabricated from the different casting solutions. The average water contact angles (CAw) of all the membranes with and without H-BFCC were tested separately and the results are presented in the table above. From the above CAw data, we can see that the contact angle of the H-BFCC composite flat sheet membrane increases with an increase in H-BFCC concentration. The CAw is as high as 123.2±3.1° for membrane sample M5 which is fairly high, compared to conventional membrane sample M1 (without H-BFCC) which was 91.6±2.1°. Clearly, the increase in CAw is due to addition of H-BFCC. The fluorine atoms in the H-BFCC are responsible for this jump in contact angle.

The average LEPw also increased with an increase in the H-BFCC concentration in the membrane matrix, the highest LEPw achieved is 380±20 Kpa for 5% of HBFCC in the casting solution (M4). This is almost double than the membrane without H-BFCC (M1). Even though there is not much difference in the average pore size of the membranes, the H-BFCC composite membranes give rise to higher LEPw compared to the membrane without H-BFCC. This is due to the higher surface contact angle (hydrophobicity) of the H-BFCC composite membranes.

No LEPw data is provided for membrane sample M5 owing to defects as will be shown later.

FTIR Analysis

Figure 16:
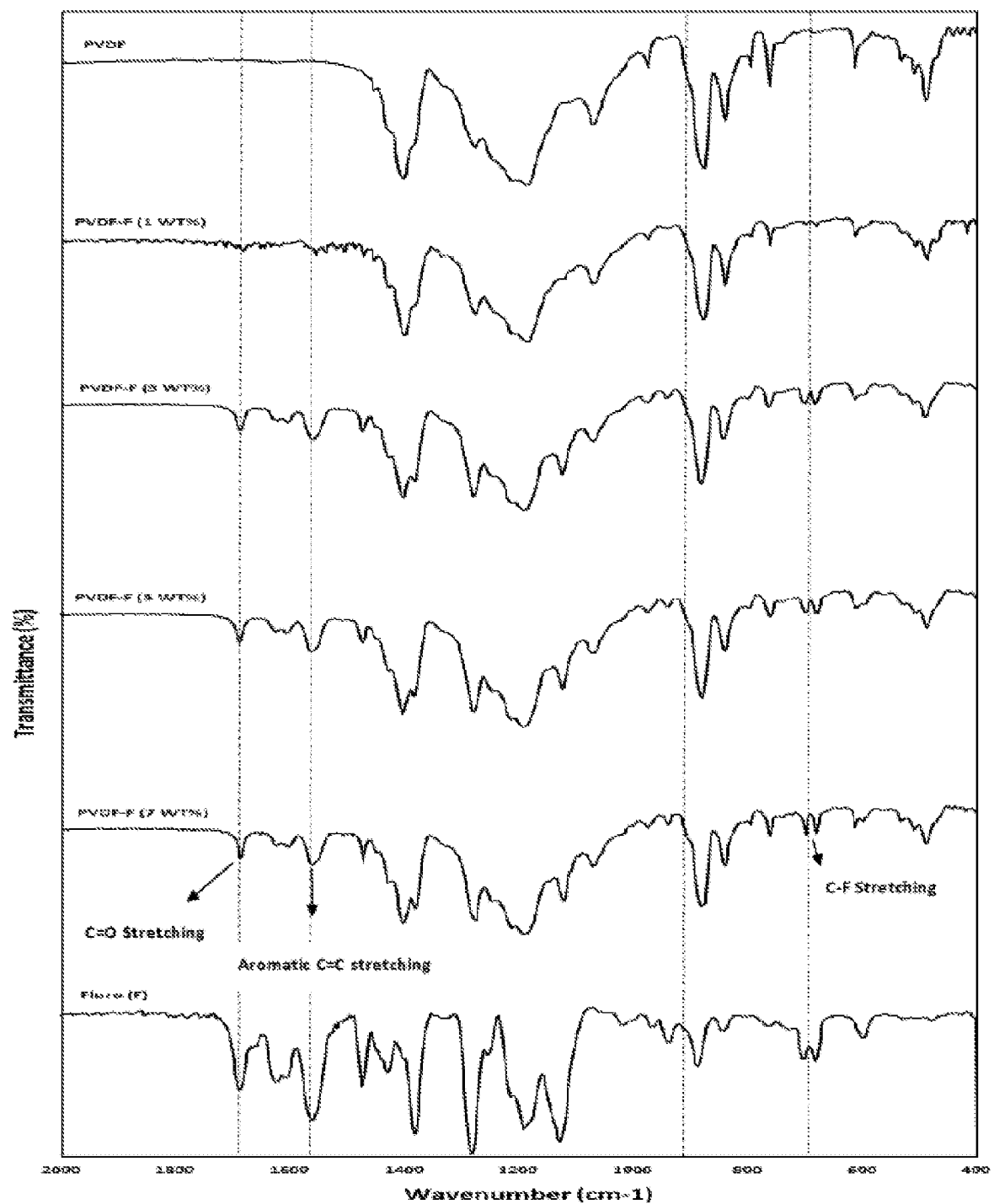
FIG. 16 is a FTIR spectrum of the control PVDF and modified PVDF membranes mentioned in Example 4.

The membranes were characterized using FTIR. FIG. 16 shows the FTIR spectra of control (PVDF), and PVDF fabricated with varying weight percentage of the H-BFCC. The spectra shows the slight increase in intensity of peaks related to H-BFCC (C=O stretching around 1687 $cm^{-1}$, C=C stretching vibrations at 1580 $cm^{-1}$ and C—F stretching vibration around 680 $cm^{-1}$) as the wt % of H-BFCC increases. The membranes fabricated with H-BFCC shows peaks for both PVDF and H-BFCC, hence confirming presence of H-BFCC in the membrane matrix.

Morphology Analysis

Figure 17:
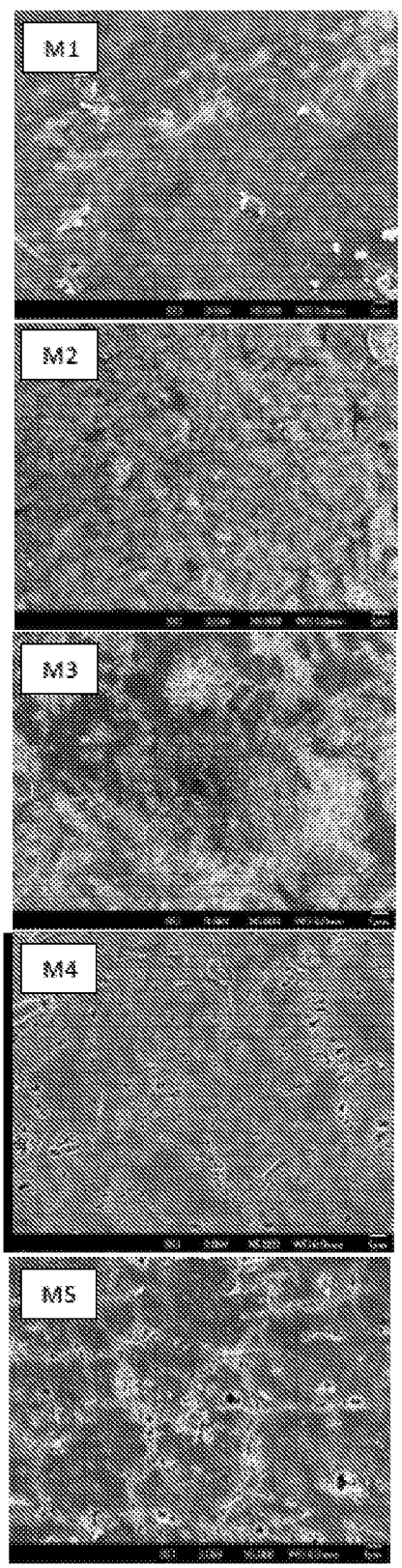
FIG. 17 are the SEM images of samples M1 to M5 mentioned in Example 4.

The Scanning Electron Microscope (SEM) images of the top layer of the membranes are shown in FIG. 17. From the SEM images, it is identified that membrane samples M2 and M3 have more porous surface than the control membrane M1. The membrane sample M4 has minimum pores on the surface and possesses minor defect on the surface. The high H-BFCC concentration membrane M5 surface shows cracks and defects on the surface.

Example 5: Characterization of Membrane Performance in Vacuum Membrane Distillation (VMD)

The membranes of Example 4 were installed within the membrane module of a VMD system with one side of the membrane in contact with hot brine stream (3.5% sodium chloride solution) that was pumped to the membrane module after heating in a feed tank. A half vacuum (−0.6 bar) was applied in the opposite (permeate) side of the membrane.

Figure 18:
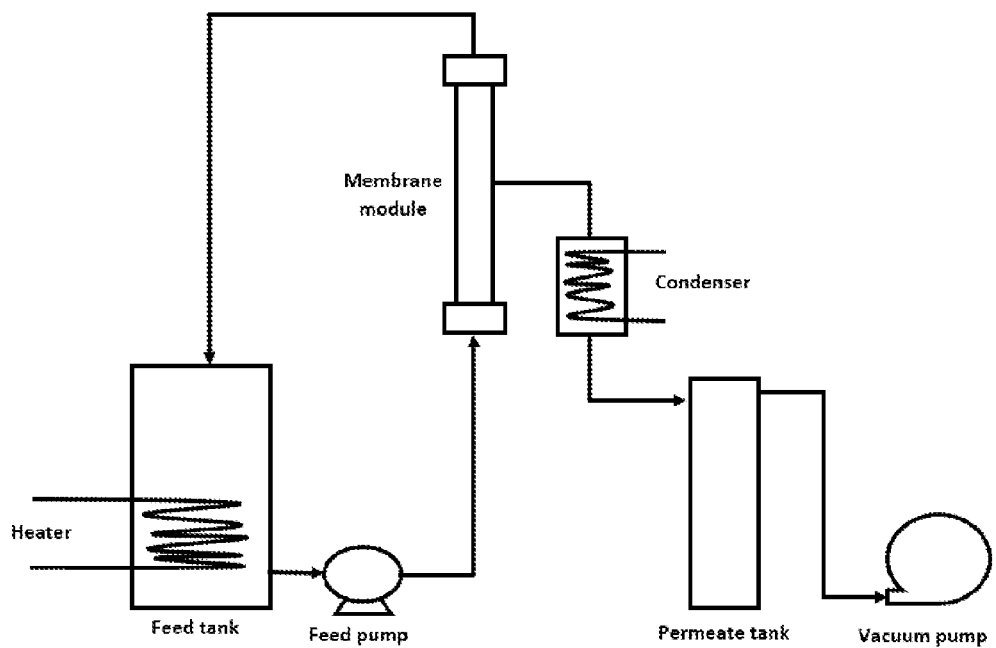
FIG. 18 is a schematic diagram of a Vacuum Membrane Distillation (VMD) system in Example 5.

Water vapour that passed through the membrane was condensed outside the membrane module using a condensor. The distillation flux was calculated by weight loss method. FIG. 18 shows a schematic diagram of the VMD system. The experiment were carried out at a constant temperature of 70° C., to investigate the effect of H-BFCC $N^1,N^3,N^5$-tris (3,5-bis(trifluoromethyl)phenyl)-$N^1,N^3,N^5$-tris(perfluoropropan-2-yl)benzene-1,3,5-tricarboxamide on performance of the membranes.

Figure 19:
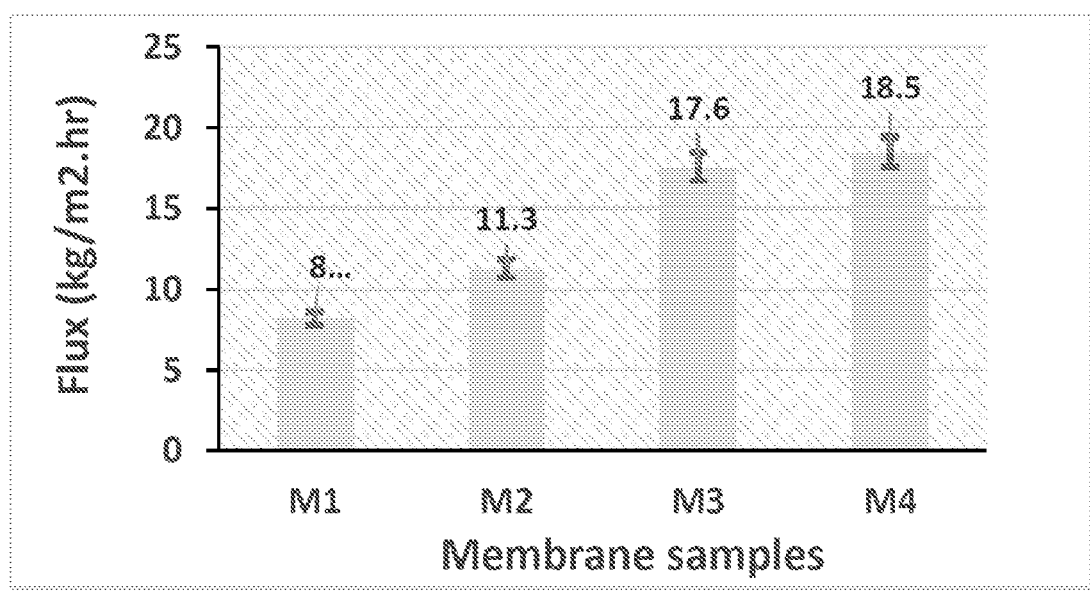
FIG. 19 shows the pure water flux of the different membrane samples tested and reported in Example 5.

The membrane distillation flux and the salt rejection factor of all membranes were tested separately using VMD process and the results are presented in a graph as shown in FIG. 19. FIG. 19 shows the effect of H-BFCC concentration on the membrane distillation flux of membrane samples M1-M4 (membrane sample M5 was not tested due to the defects on the surface). The pure water flux increased with an increase in H-BFCC concentration in the casting solution from 1% and 5%. This is mainly due to the increased surface hydrophobicity of the membranes. The highest flux achieved for the H-BFCC composite flat sheet membrane is 18.5 $kg/m^2 \cdot hr$ at 70° C. for the membrane that was fabricated from casting solution comprising 5% H-BFCC.

The average salt rejection of the membranes was determined by measuring the conductivity. The salt rejection of all the membranes are >99%.

Example 6: One-Pot Preparation of Highly Hydrophobic, Thermally Stable and Hyper-Branched Fluorinated Chemical Compound-Based Hollow Fiber Membrane for Steam and Vapour Transportation 3,5-bis(trifluoromethyl)aniline and heptafluoro-2-iodopropane in 1:1 molar ratio were dissolved in DMAc and stirred in a reaction vessel at a temperature of 80° C. for 2 hours. after two hours, trimesoyl chloride (TMC) was then added to the solution. The ratio of TMC to the intermediate secondary amine was calculated to be 1:3. The solution was left to stir under a controlled temperature of 80° C. for another 20-30 mins, during which the highly hydrophobic H-BFCC compound, $N^1,N^3,N^5$-tris(3,5-bis(trifluoromethyl)phenyl)-$N^1,N^3,N^5$-tris(perfluoropropan-2-yl)benzene-1,3,5-tricarboxamide will be formed.

Base polymer, PVDF, and other additives (PVP/PEG as pore forming agent and Ethanol/Water as nonsolvent) were added to the reaction vessel and stirred for 18 hrs to prepare a casting solution comprising the highly hydrophobic and thermally stable H-BFCC. The prepared casting solution was transferred to a solution holding tank and degassed at a vacuum pressure of −0.8 bar for 0.5 hrs. After degassing, nitrogen gas was purged into the tank to create an inert atmosphere and to push the casting solution to the polymer pump for membrane fabrication. The composition of the casting solution is presented in Table 3.

TABLE 3

Composition of the membrane casting solution used in Example 6

| Sample ID | PVDF-Kynar-761 (wt %) | PVP-K30 (wt %) | 3,5-bis(trifluoromethyl)aniline | Heptafluoro-2-iodopropane | trimesoyl chloride (TMC) | DMAC (wt %) | Ethanol (wt %) |
|---|---|---|---|---|---|---|---|
| M1 | 21 | 10 | 0.5 | 0.5 | 3 | 63 | 2 |

Bore liquid comprising DMAc and water in 4:1 volume ratio was prepared and poured into the bore liquid tank. The casting solution and the bore liquid were pumped to a spinneret (OD 1.2 mm, ID 0.6 mm). The air gap was fixed at 10 mm. The hollow fiber membranes were fabricated at around 25° C. and at around 70% relative humidity with a take up speed of 0.26 m/s.

The hollow fiber membrane turned opaque soon after coming into contact with water which indicates that the coagulation and precipitation of the base polymer and hydrophobic additive from the solution and finally a translucent, white hollow fiber membrane was formed. The membrane was then collected from the winder and left inside a water tank (post coagulation tank) for 24 hrs to washout the residual DMAc and PVP that was not removed from the solution at the point of coagulation.

Following the rinsing process, the membrane was subjected to a post treatment process whereby the membrane was washed with water, ethanol and hexane to remove any hydrophilic substance and additives from the membrane matrix/surface. The post-treated membrane was dried at room temperature for 24 hrs before testing.

The prepared membrane was characterized in terms of outer diameter OD, inner diameter ID, pore size, LEPw and CAw. The results are shown in Table 4.

TABLE 4

Membrane characterization data of Example 6

| Membrane ID | OD (mm) | ID (mm) | Pore size (μm) | LEPw (kPa) | CAw (°) |
|---|---|---|---|---|---|
| M1 | 1.2 | 0.6 | 0.09 ± 0.02 | 350 ± 10 | 105.6 ± 2.1 |

Morphology Analysis

Figure 20:
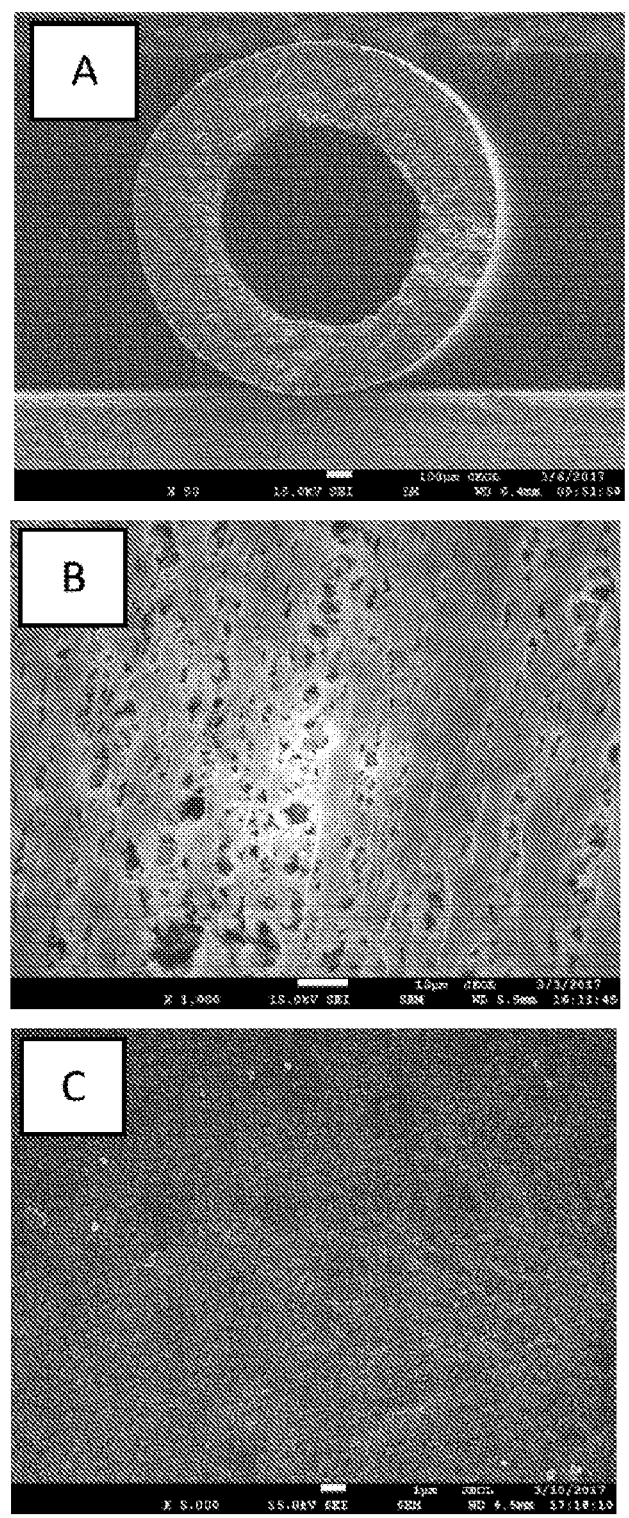
FIG. 20 are the SEM images of cross section (A), inner surface (B) and outer surface (C) of the membrane in Example 6.

The SEM images of the cross section, inner surface and outer surface of the membrane are presented in FIG. 20. From the cross section, it can be identified that the membrane has a sponge-like structure throughout the membrane matrix.

Performance in VMD

The membrane distillation flux and salt rejection factor of the membrane were tested separately using the VMD system and same operating conditions as described in Example 5. The clean water flux was found to be 14.3 kg/m²·hr and the salt rejection was >99.9% as shown in Table 5 below.

TABLE 5

Membrane performance data

| Clean water flux (kg/m²hr) | Salt rejection (%) |
|---|---|
| 14.3 | >99.9 |

Example 7: Synthesis of Fluoro-Graphene

Ethylenediamine functionalized graphene (Amine-GnP) and heptafluoro-2-iodopropane were dissolved in DMAc and reacted under continuous stirring at approximately 80° C. for 1 to 2 hr to obtain a hyper-branched fluorinated graphene (Fluoro-GnP).

The above is a description of the subject matter the inventors regard as the invention and is believed that those skilled in the art can and will design alternative embodiments that include of this invention as set forth in the following claims.

The invention claimed is:

1. A hyper-branched compound represented by the general structure (I):

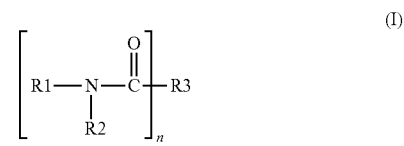

(I)

wherein
n is an integer representing the number of substitutions and wherein the integer is 1 to 3;

R2 is a fluorinated hydrocarbon having the following structure (II):

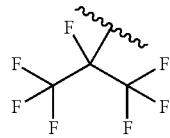

(II)

R1 is a fluorinated phenyl; and

R3 is a phenyl substituted with the n substitutions when n is 2 or 3, or a phenyl substituted with at least one fluorine when n is 1.

2. The hyper-branched compound of claim 1, wherein R1 is fluorinated phenyl selected from the group consisting of 3, 5-bis(trifluoromethyl)phenyl and 2, 4, 5-trifluorophenyl.

3. The hyper-branched compound of claim 1, wherein R3 is phenyl substituted at positions 2, 4, 5 with fluorine and substituted at position 3 with —OCH$_3$, when n is 1.

4. The hyper-branched compound of claim 2, wherein the compound is N$^1$,N$^3$,N$^5$-tris(3,5-bis(trifluoromethyl)phenyl)-N$^1$,N$^3$,N$^5$-tris(perfluoropropan-2-yl)benzene-1,3,5-tricarboxamide when n is 3 and R1 is 3,5-bis(trifluoromethyl)phenyl, and represented by the following structural formula (A):

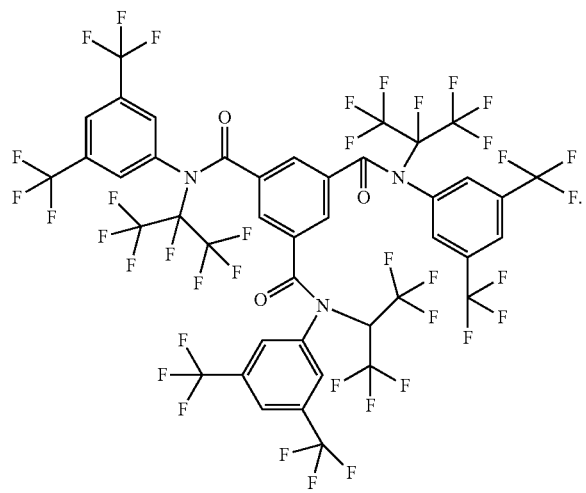

(A)

5. The hyper-branched compound of claim 2, wherein the compound is N$^1$,N$^3$,N$^5$-tris(perfluoropropan-2-yl)-N$^1$,N$^3$,N$^5$-tris(2,4,5-trifluorophenyl)benzene-1,3,5-tricarboamide, when n is 3, R1 is 2, 4, 5-trifluorophenyl, and represented by the following structural formula (B):

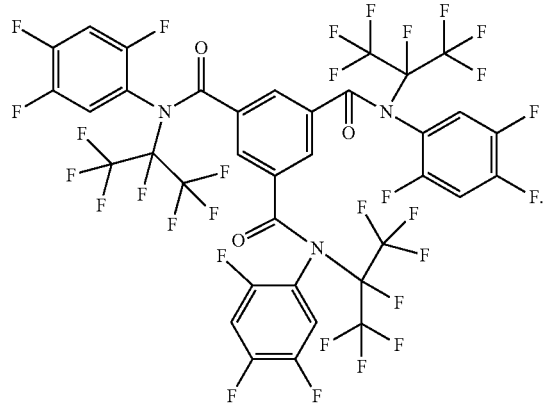

(B)

6. The hyper-branched compound of claim 3, wherein the compound is 2,4,5-trifluoro-3-methoxy-N-(perfluoropropan-2-yl)-N-(2,4,5-trifluorophenyl)benzamide, represented by the following structural formula ©:

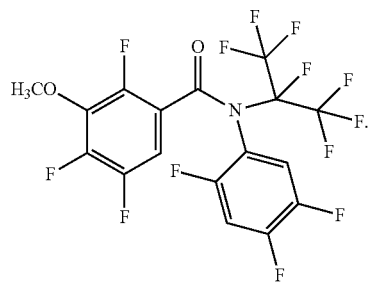

(C)

7. A method of preparing a hyper-branched compound of claim 1, the method comprising:

contacting a fluorinated first reactant containing at least one primary amine group with a fluorinated second reactant containing at least one amine reactive group in the presence of a solvent to form a fluorinated intermediate containing at least one secondary amine group; and contacting the fluorinated intermediate with a third reactant containing at least one carbonyl chloride group to form at least one amide linkage between the fluorinated intermediate and the third reactant to form a fluorinated amide-containing hyper-branched compound comprising n substitutions, wherein n is 1 to 3.

8. The method of claim 7, wherein the amine reactive group is iodine.

9. The method of claim 7, wherein the first reactant is fluorinated aniline.

10. The method of claim 9, wherein the first reactant is selected from the group consisting of 3,5-bis(triflurormethyl)aniline and 2,4,5-trifluoroaniline.

11. The method of claim 8, wherein the second reactant is heptafluoro-2-iodopropane.

12. The method of claim 7, wherein the third reactant is selected from the group consisting of trimesoyl chloride and 2,4,5-trifluoro-3-methoxybenzoyl chloride.

13. The method of claim 7, wherein the first reactant is 3,5-bis(triflurormethyl)aniline, the second reactant is heptafluoro-2-iodopropane, and the third reactant is trimesoyl chloride to form the fluorinated amide-containing compound with 3 n substitutions, represented by the following structural formula (A):

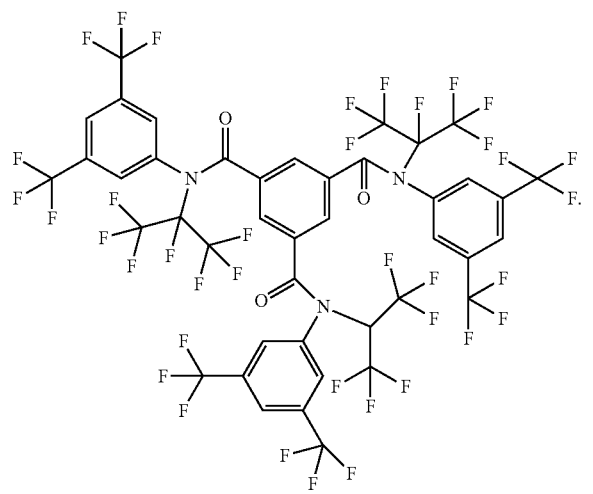

(A)

14. The method of claim 7, wherein the first reactant is 2,4,5-trifluoroaniline, the second reactant is heptafluoro-2-iodopropane, and the third reactant is trimesoyl chloride to form the fluorinated amide-containing compound with 3 n substitutions, represented by the following structural formula (B):

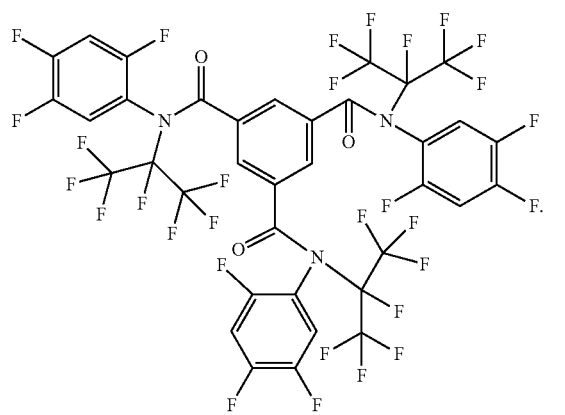

(B)

15. The method of claim 7, wherein the first reactant is 2,4,5-trifluoroaniline, the second reactant is heptafluoro-2-iodopropane, and the third reactant is 2,4,5-trifluoro-3-methoxybenzoyl chloride to form the fluorinated amide-containing compound with 1 n substitution, represented by the following structural formula ©:

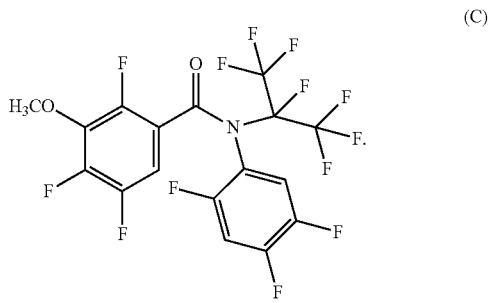 [SMILES: COc1c(F)c(F)cc(C(=O)N(c2cc(F)c(F)cc2F)C(F)(C(F)(F)F)C(F)(F)F)c1F]

(C)

16. A membrane comprising the hyper-branched compound of claim 1.

17. The membrane of claim 16 for use in a membrane distillation process.

* * * * *